United States Patent
Whittingham et al.

(10) Patent No.: US 8,530,388 B2
(45) Date of Patent: Sep. 10, 2013

(54) CYCLOPENTADIONE DERIVED HERBICIDES

(75) Inventors: William Guy Whittingham, Bracknell (GB); Christopher John Mathews, Bracknell (GB); Jeffrey Steven Wailes, Bracknell (GB); Stephane André Marie Jeansmart, Stein (CH); Louisa Robinson, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 0 days.

(21) Appl. No.: 13/145,219

(22) PCT Filed: Jan. 18, 2010

(86) PCT No.: PCT/EP2010/050490
§ 371 (c)(1), (2), (4) Date: Jul. 19, 2011

(87) PCT Pub. No.: WO2010/081894
PCT Pub. Date: Jul. 22, 2010

(65) Prior Publication Data
US 2011/0275515 A1    Nov. 10, 2011

(30) Foreign Application Priority Data
Jan. 19, 2009  (GB) .................................. 0900864.0

(51) Int. Cl.
*A01N 43/40* (2006.01)
*A01N 43/12* (2006.01)
*C07D 213/02* (2006.01)
*C07D 333/50* (2006.01)

(52) U.S. Cl.
USPC ............... 504/244; 546/339; 549/41; 549/49; 549/51; 504/288; 504/289

(58) Field of Classification Search
USPC ........... 546/339; 504/244, 288, 289; 549/29, 549/41, 49, 51
See application file for complete search history.

(56) References Cited

U.S. PATENT DOCUMENTS
2010/0210466 A1    8/2010 Muehlebach et al.

FOREIGN PATENT DOCUMENTS
| DE | 19935963 | 2/2001 |
| DE | 10326386 | 12/2004 |
| DE | 102006000971 | 7/2007 |
| WO | 9948869 | 9/1999 |
| WO | 2008071405 | 6/2008 |
| WO | 2009019015 | 2/2009 |

*Primary Examiner* — Golam M M Shameem
(74) *Attorney, Agent, or Firm* — R. Kody Jones

(57) ABSTRACT

Compounds of formula (I), wherein the substituents are as defined in claim 1, are suitable for use as herbicides.

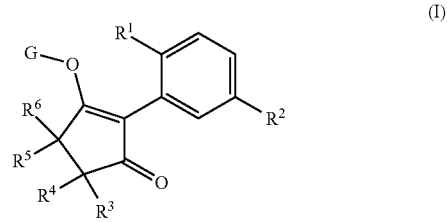

(I)

13 Claims, No Drawings

CYCLOPENTADIONE DERIVED HERBICIDES

This application is a 371 of International Application No. PCT/EP2010/050490 filed Jan. 18, 2010 which claims priority to GB 0900864.0 filed Jan. 19, 2009, the contents of which are incorporated herein by reference.

The present invention relates to novel, herbicidally active cyclic diones, and derivatives thereof, to processes for their preparation, to compositions comprising those compounds, and to their use in controlling weeds, especially in crops of useful plants, or in inhibiting plant growth.

Cyclopentanediones having herbicidal action are described, for example, in U.S. Pat. No. 4,283,348, U.S. Pat. No. 4,338,122, U.S. Pat. No. 4,436,666, WO99/48869, WO01/79204 and WO01/098288.

Novel cyclopentanedione compounds, having improved herbicidal and growth-inhibiting properties have now been found. The present invention accordingly relates to compounds of formula I

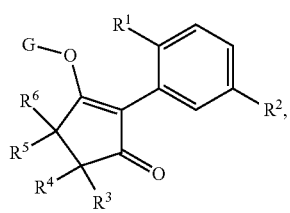

(I)

wherein
$R^1$ is ethyl, difluoromethoxy, trifluoromethoxy or cyclopropyl,
$R^2$ is optionally substituted aryl or optionally substituted heteroaryl,
$R^3$, $R^4$, $R^5$ and $R^6$ are independently of each other, hydrogen, $C_1$-$C_4$alkyl, $C_2$-$C_4$alkenyl, $C_2$-$C_4$alkynyl, $C_1$-$C_3$haloalkyl, $C_2$-$C_4$haloalkenyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl $C_1$-$C_3$alkyl, $C_3$-$C_6$cycloalkyl in which a methylene group is optionally replaced by an oxygen or sulfur atom and wherein the ring is optionally substituted once or twice by halogen, $C_1$-$C_2$alkyl or $C_1$-$C_2$alkoxy, or $C_3$-$C_6$cycloalkyl$C_1$-$C_3$alkyl optionally substituted by halogen, $C_1$-$C_2$alkyl or $C_1$-$C_2$alkoxy,
or $R^3$ and $R^4$, or $R^5$ and $R^6$, together with the carbon atoms to which they are attached form a three- to seven-membered carbocyclic ring, in which a methylene group is optionally replaced by an oxygen or sulfur atom and wherein the ring is optionally substituted once or twice by halogen, $C_1$-$C_2$alkyl or $C_1$-$C_2$alkoxy,
or $R^4$ and $R^5$, together with the carbon atoms to which they are attached form a three- to seven-membered saturated carbocyclic ring, in which a methylene group is optionally replaced by an oxygen or sulfur atom and wherein the ring is optionally substituted once or twice by halogen, $C_1$-$C_2$alkyl or $C_1$-$C_2$alkoxy,
or $R^4$ and $R^5$, together with the carbon atoms to which they are attached form a five- to seven-membered unsaturated carbocyclic ring, wherein the ring is optionally substituted once or twice by halogen, $C_1$-$C_2$alkyl or $C_1$-$C_2$alkoxy,
and
G is hydrogen or an agriculturally acceptable metal, ammonium, sulfonium or latentiating group.

In the substituent definitions of the compounds of the formula I, each alkyl moiety either alone or as part of a larger group (such as alkoxy, alkoxyalkyl, alkylthioalkyl) is a straight or branched chain and is, for example, methyl, ethyl, n-propyl and isopropyl as well as n-butyl, isobutyl and t-butyl.

The alkenyl and alkynyl radicals having 2 to 4 carbon atoms can be straight or branched and can contain more than 1 double or triple bond. Examples are vinyl, allyl, propargyl, butenyl, butadienyl and butynyl.

Haloalkyl groups are alkyl groups which are substituted with one or more of the same or different halogen atoms and are, for example, $CF_3$, $CF_2C_1$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

In the context of the present specification the term "aryl" preferably refers to phenyl and naphthyl. The term "heteroaryl" refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidinyl, triazinyl, thienyl, furyl, oxazolyl, isoxazolyl, 2,1,3-benzoxadiazolyl and thiazolyl.

Cycloalkyl includes preferably cyclopropyl, cyclobutyl, cyclopentyl and cyclohexyl.

Carbocyclic rings such as those formed together by $R^5$ and $R^6$ include cycloalkyl and cycloalkenyl groups with 3 to 7 atoms, optionally including one or more, preferably 1 or 2 heteroatoms selected from O and S leading to heterocycles such as 1,3-dioxolane, oxetane, furan and tetrahydrofuran.

Agriculturally acceptable metals are alkali metal or alkaline earth metal ions, for example sodium, potassium, magnesium and calcium ions, and transition metal ions, for example copper and iron atoms. Suitable ammonium ions are $NH_4^+$, alkylammonium, dialkylammonium, triakylammonium and tetraalkylammonium ions. Suitable sulfonium ions are trialkylsulfonium ions, for example trimethylsulfonium ions.

It should be understood that in those compounds of formula I, where G is a metal, ammonium or sulfonium as mentioned above and as such represents a cation, the corresponding negative charge is largely delocalised across the O—C=C—C=O unit.

When present, the optional substituents on aryl and heteroaryl are selected independently, from halogen, nitro, cyano, rhodano, isothiocyanato, $C_{1-6}$ alkyl, $C_{1-6}$ haloalkyl, $C_{1-6}$ alkoxy-($C_{1-6}$)alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkylsilyl($C_{1-6}$) alkoxy, $C_{1-6}$ alkoxycarbonyl($C_{1-10}$)alkoxy, $C_{1-10}$ haloalkoxy, aryl($C_{1-4}$)alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{3-10}$ alkenyloxy, $C_{3-10}$ alkynyloxy, mercapto, $C_{1-10}$ alkylthio, $C_{1-10}$ haloalkylthio, aryl($C_{1-4}$)alkylthio, $C_{3-7}$ cycloalkylthio (where the cycloalkyl group is optionally substituted with $C_{1-6}$ alkyl or halogen), tri($C_{1-4}$)-alkylsilyl($C_{1-6}$)-alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, tri($C_{1-4}$)alkylsilyl, aryldi($C_{1-4}$)-alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)-aminocarbonyl, N—($C_{1-3}$ alkyl)-N—($C_{1-3}$ alkoxy) aminocarbonyl, $C_{1-6}$ alkylcarbonyloxy, arylcarbonyloxy, di($C_{1-6}$)alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include arylcarbonylamino (where the aryl group is substituted by $C_{1-6}$ alkyl or halogen), ($C_{1-6}$)alkoxycarbonylamino($C_{1-6}$)alkoxycarbonyl-N—($C_{1-6}$)alkylamino, aryloxycarbonylamino (where the aryl group is substituted by $C_{1-6}$ alkyl or halogen), aryloxycarbonyl-N—($C_{1-6}$)alkylamino, (where the aryl group is substituted by $C_{1-6}$ alkyl or halogen), arylsulphonylamino (where the aryl group is substituted by $C_{1-6}$ alkyl or halogen), arylsulphonyl-N—($C_{1-6}$) alkylamino (where the aryl group is substituted by $C_{1-6}$ alkyl or halogen), aryl-N—($C_{1-6}$)alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonylamino, di($C_{1-6}$)alkylaminocarbonylamino, arylaminocarbonylamino where the aryl group is substituted by $C_{1-6}$ alkyl or halogen), aryl-N—($C_{1-6}$)alkylamino-carbonylamino where the aryl group is substituted by $C_{1-6}$ alkyl or halogen), $C_{1-6}$ alkylaminocarbonyl-N—($C_{1-6}$)alkylamino, di($C_{1-6}$)alkylaminocarbonyl-N—($C_{1-6}$)alkylamino, arylaminocarbonyl-N—($C_{1-6}$)alkylamino where the aryl group is substituted by $C_{1-6}$ alkyl or halogen) and aryl-N—($C_{1-6}$)alkylaminocarbonyl-N—($C_{1-6}$)alkylamino where the aryl group is substituted by $C_{1-6}$ alkyl or halogen).

For substituted aryl moieties and heteroaryl groups it is particularly preferred that one or more substituents are independently selected from halogen, in particular chloro, cyano, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, nitro and cyano. It is to be understood that dialkylamino substituents include those where the dialkyl groups together with the N atom to which they are attached form a five, six or seven-membered heterocyclic ring which may contain one or more further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, thiomorpholine and morpholine each of which may be substituted by one or two independently selected ($C_{1-6}$)alkyl groups.

The invention relates also to the salts which the compounds of formula I are able to form with amines, alkali metal and alkaline earth metal bases or quaternary ammonium bases.

Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$-alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula $[N(R_aR_bR_cR_d)]OH$ wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

The latentiating groups G are selected to allow their removal by one or a combination of biochemical, chemical or physical processes to afford compounds of formula I where G is H before, during or following application to the treated area or plants. Examples of these processes include enzymatic cleavage, chemical hydrolysis and photolysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

The latentiating group G is preferably selected from the groups —C($X^a$)—$R^a$, C($X^b$)—$X^c$—$R^b$, C($X^d$)—N($R^c$)—$R^d$, —SO$_2$—$R^e$, —P($X^e$)($R^f$)—$R^g$ or CH$_2$—$X^f$—$R^h$, wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_2$-$C_{18}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{18}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{18}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

Preferably, G denotes hydrogen, an alkali metal or alkaline earth metal or a latentiating group.

In particular, the latentiating group G is a group —C($X^a$)—$R^a$ or —C($X^b$)—$X^c$—$R^b$, and the meanings of $X^a$, $R^a$, $X^b$, $X^c$ and $R^b$ are as defined above.

G as hydrogen is especially preferred.

Depending on the nature of the substituents G, $R^1$, $R^2$, $R^3$, $R^4$, $R^5$, $R^6$, $R^7$ and $R^8$, compounds of formula I may exist in different isomeric forms. When G is hydrogen, for example, compounds of formula I may exist in different tautomeric forms. Also, when substituents contain double bonds, cis- and trans-isomers can exist. This invention covers all such isomers and tautomers and mixtures thereof in all proportions. These isomers, too, are within the scope of the claimed compounds of the formula I.

It should be mentioned again that in those compounds of formula I, where G is a metal, ammonium (such as $NH_4^+$; N(alkyl)$_4$+) or sulfonium (such as S(alkyl)$_3$+) cation, the corresponding negative charge is largely delocalised across the O—C=C—C=O unit.

Preferably, $R^1$ is ethyl.

Preferably, $R^2$ is optionally substituted phenyl or optionally substituted pyridyl. In particular, $R^2$ is phenyl substituted one to three times by fluorine, chlorine, bromine, methoxy, methyl, cyano or trifluoromethyl.

Preferably, $R^3$ and $R^4$ are independently, hydrogen or $C_1$-$C_3$alkyl,

Preferably, $R^5$ and $R^6$ are independently of each other hydrogen, $C_1$-$C_3$alkyl, $C_1$-$C_3$alkoxy$C_1$-$C_3$alkyl, optionally substituted $C_3$-$C_6$cycloalkyl in which a ring carbon atom is optionally replaced by an oxygen or sulfur atom and wherein the ring is optionally substituted once or twice by $C_1$-$C_2$ alkyl or $C_1$-$C_2$ alkoxy, or $R^5$ and $R^6$ together with the carbon atom to which they are attached form an optionally substituted three- to seven membered carbocyclic ring, in which a ring carbon atom is optionally replaced by an oxygen or sulfur atom and wherein the ring is optionally substituted once or twice by $C_1$-$C_2$alkyl or $C_1$-$C_2$ alkoxy. More preferably, $R^5$ and $R^6$ are independently of each other hydrogen, $C_1$-$C_3$alkyl, $C_1$-$C_3$alkoxy$C_1$-$C_3$alkyl, or $R^5$ and $R^6$ together with the carbon atom to which they are attached form an optionally substituted five- or six-membered carbocyclic ring, in which a ring carbon atom is optionally replaced by an oxygen atom, and wherein the ring is optionally substituted once or twice by $C_1$-$C_2$alkyl or $C_1$-$C_2$ alkoxy.

Preferably, G is hydrogen or a group —C($X^a$)—$R^a$ or —($X^b$)—$X^c$—$R^b$, wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{18}$-aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $X^a$, $X^b$ and $X^c$ are independently of each other oxygen or sulfur.

More preferably, G is hydrogen.

In another preferred group of compounds, $R^1$ is ethyl, trifluoromethoxy or cyclopropyl, $R^2$ is phenyl substituted one to three times by fluorine, chlorine, bromine, methoxy, methyl or trifluoromethyl, or R1 is naphthyl, $R^3$, $R^4$, $R^5$ and $R^6$ are hydrogen, or $R^5$ and $R^6$ together with the carbon atom to which they are attached form an optionally substituted three- to seven membered carbocyclic ring, in which a ring carbon atom is optionally replaced by a sulfur atom.

A compound of formula (I) wherein G is $C_1$-$C_8$ alkyl, $C_2$-$C_8$ haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating a compound of formula (A), which is a compound of formula (I) wherein G is H, with a reagent G-Z, wherein G-Z is alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$ alkyl sulfonate, or a di-$C_1$-$C_8$-alkyl sulfate, or with a $C_3$-$C_8$ alkenyl halide, or with a $C_3$-$C_8$ alkynyl halide, or with an acylating agent such as a carboxylic acid, HO—$C(X^a)R^a$, wherein $X^a$ is oxygen, an acid chloride, Cl—$C(X^a)R^a$, wherein $X^a$ is oxygen, or acid anhydride, $[R^aC(X^a)]_2O$, wherein $X^a$ is oxygen, or an isocyanate, $R^cN$=$C$=$O$, or a carbamoyl chloride, Cl—$C(X^d)$—$N(R^c)$—$R^d$ (wherein $X^d$ is oxygen and with the proviso that neither $R^c$ or $R^d$ is hydrogen), or a thiocarbamoyl chloride Cl—$C(X^d)$—$N(R^c)$—$R^d$ (wherein $X^d$ is sulfur and with the proviso that neither $R^c$ or $R^d$ is hydrogen) or a chloroformate, Cl—$C(X^b)$—$X^c$—$R^b$, (wherein $X^b$ and $X^c$ are oxygen), or a chlorothioformate Cl—$C(X^b)$—$X^c$—$R^b$ (wherein $X^b$ is oxygen and $X^c$ is sulfur), or a chlorodithioformate Cl—$C(X^b)$—$X^c$—$R^b$, (wherein $X^b$ and $X^c$ are sulfur), or an isothiocyanate, $R^cN$=$C$=$S$, or by sequential treatment with carbon disulfide and an alkylating agent, or with a phosphorylating agent such as a phosphoryl chloride, Cl—$P(X^e)(R^f)$—$R^g$ or with a sulfonylating agent such as a sulfonyl chloride Cl—$SO_2$—$R^e$, preferably in the presence of at least one equivalent of base. Those skilled in the art will recognise that when a compound of formula (A) contains an unsymmetrical dione (for example, where substituents $R^3$ and $R^4$ are different to $R^5$ and $R^6$), these reactions may produce, in addition to a compound of formula (1), a second compound of formula (1A). This invention covers both a compound of formula (1) and a compound of formula (1A), together with mixtures of these compounds in any ratio.

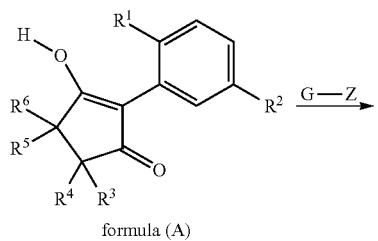

formula (A)

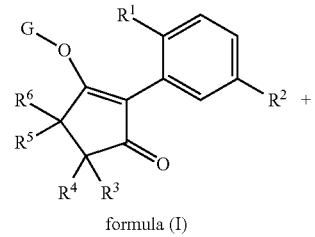

formula (I)

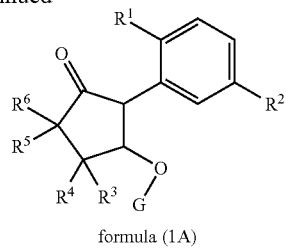

formula (1A)

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425; H. Born et al., J. Chem. Soc., (1953), 1779; M. Constantino et al., Synth. Commun., (1992), 22 (19), 2859; Y. Tian et al., Synth. Commun., (1997), 27 (9), 1577, S. Chandra Roy et al., Chem. Letters, (2006), 35 (1) 16, and P. Zubaidha et al., Tetrahedron Lett., (2004), 45, 7187.

The O-acylation of cyclic 1,3-diones may be effected by procedures similar to those described, for example, by R Haines, U.S. Pat. No. 4,175,135, and by T. Wheeler, U.S. Pat. No. 4,551,547, U.S. Pat. No. 4,422,870, U.S. Pat. No. 4,659,372 and U.S. Pat. No. 4,436,666. Typically diones of formula (A) may be treated with the acylating agent in the presence of at least one equivalent of a suitable base, optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595 and T. Isobe and T. Ishikawa, J. Org. Chem., (1999), 64 (19), 6984.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in the presence of at least one equivalent of base, for example by the procedure of C. Kowalski and K. Fields, J. Org. Chem., (1981), 46, 197.

A compound of formula (A) may be prepared by the cyclisation of a compound of formula (B), wherein R is hydrogen or an alkyl group, preferably in the presence of an acid or base, and optionally in the presence of a suitable solvent, by analogous methods to those described by T. Wheeler, U.S. Pat. No. 4,283,348. The compounds of formula (B) have been particularly designed as intermediates in the synthesis of the compounds of the formula (I). A compound of formula (B) wherein R is hydrogen may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

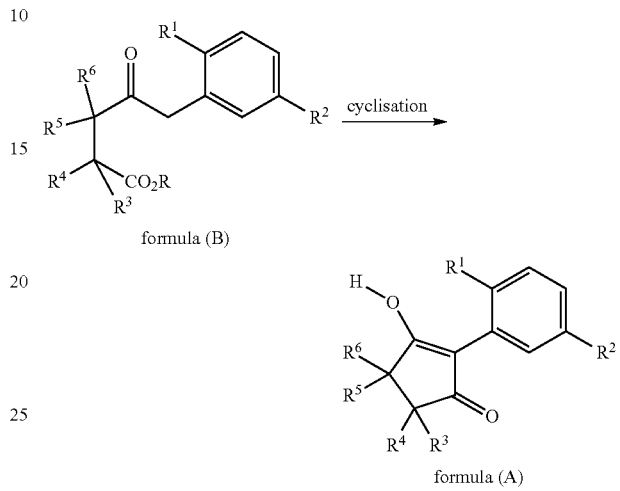

A compound of formula (B) wherein R is alkyl (preferably methyl or ethyl), may be cyclised under basic conditions, preferably in the presence of at least one equivalent of a strong base such as potassium tert-butoxide, lithium diisopropylamide or sodium hydride and in a solvent such as tetrahydrofuran, dimethylsulfoxide or N,N-dimethylformamide.

A compound of formula (B), wherein R is H, may be prepared by saponification of a compound of formula (C) wherein R' is alkyl (preferably methyl or ethyl), under standard conditions, followed by acidification of the reaction mixture to effect decarboxylation, by similar processes to those described, for example, by T. Wheeler, U.S. Pat. No. 4,209,532.

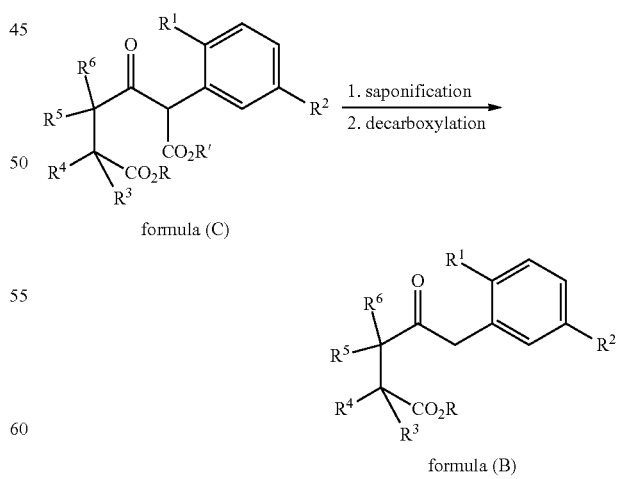

A compound of formula (B), wherein R is H, may be esterified to a compound of formula (B), wherein R is alkyl, under known conditions, for example by heating with an alkyl alcohol, ROH, in the presence of an acid catalyst.

A compound of formula (C), wherein R is H, may be prepared by treating a compound of formula (D) with a suitable base (such as potassium tert-butoxide, sodium bis(trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (E):

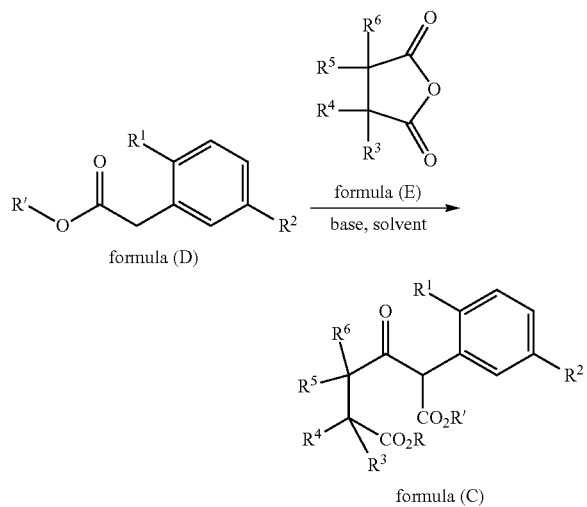

Compounds of formula (E) are known compounds, or may be prepared from known compounds by known methods.

A compound of formula (D) may be prepared from a compound of formula (F) by treatment with an alcohol, R'OH, in the presence of a suitable base. Preferably the alcohol is methanol and the base is sodium methoxide.

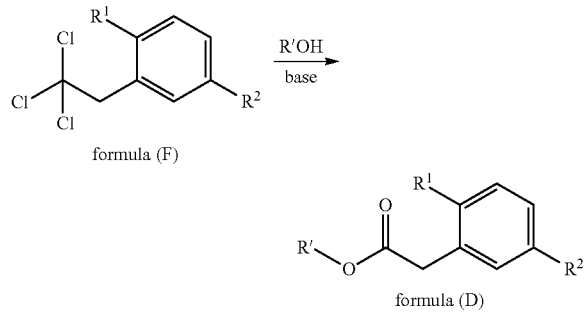

A compound of formula (F) may be prepared by Meerwein arylation of an aniline of formula (G) with vinylidene chloride under known conditions (see, for example C. Rondestvedt, Org. Reaction, (1976), 24, 225; M. Doyle et al., J. Org. Chem., (1977), 42 (14), 2431).

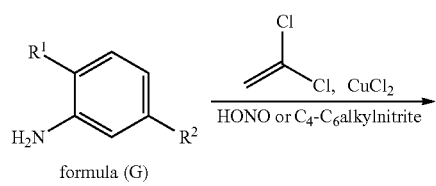

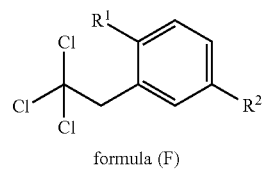

A compound of formula (G) may be prepared by reduction of a compound of formula (H) under known conditions, for example, by catalytic hydrogenation, or by using a metal such as iron or zinc powder in the presence of a suitable acid (such as acetic acid or hydrochloric acid).

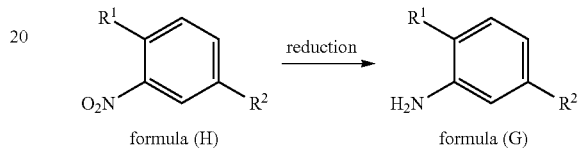

A compound of formula (H) may be prepared from an aryl halide of formula (J), wherein Hal represents a chlorine, bromine or iodine, or is a pseudohalide such as trifluoromethanesulfonyl, by reaction with an aryl- or heteroarylboronic acid of formula $R^2$—$B(OH)_2$, an aryl- or heteroarylboronate ester, $R^2$—$B(OR")_2$, wherein $R^2$—$B(OR")_2$ represents a cyclic boronate ester derived from a 1,2- or a 1,3-alkane diol such as pinacol, 2,2-dimethyl-1,3-propanediol and 2-methyl-2,4-pentanediol, or a metal (especially potassium) aryl-, or heteroaryltrifluoroborate salt, $M^+[R^3$—$BF_3]^-$ in the presence of a suitable palladium catalyst, a suitable ligand and a suitable base in the presence of a suitable solvent, under Suzuki-Miyaura conditions (see, for example K. Billingsley and S. Buchwald, J. Am. Chem. Soc., (2007), 129, 3358-3366; H. Stefani, R. Cella and A. Vieira, Tetrahedron, (2007), 63, 3623-3658; N. Kudo, M. Perseghini and G. Fu, Angew. Chem. Int. Ed., (2006), 45, 1282-1284; A. Roglans, A. Pla-Quintana and M. Moreno-Mañas, Chem. Rev., (2006), 106, 4622-4643; J-H Li, Q-M Zhu and Y-X Xie, Tetrahedron (2006), 10888-10895; S. Nolan et al., J. Org. Chem., (2006), 71, 685-692; M. Lysén and K. Köhler, Synthesis, (2006), 4, 692-698; K. Anderson and S. Buchwald, Angew. Chem. Int. Ed., (2005), 44, 6173-6177; Y. Wang and D. Sauer, Org. Lett., (2004), 6 (16), 2793-2796; I. Kondolff, H. Doucet and M, Santelli, Tetrahedron, (2004), 60, 3813-3818; F. Bellina, A. Carpita and R. Rossi, Synthesis (2004), 15, 2419-2440; H. Stefani, G. Molander, C-S Yun, M. Ribagorda and B. Biolatto, J. Org. Chem., (2003), 68, 5534-5539; A. Suzuki, Journal of Organometallic Chemistry, (2002), 653, 83; G. Molander and C-S Yun, Tetrahedron, (2002), 58, 1465-1470; G. Zou, Y. K. Reddy and J. Falck, Tetrahedron Lett., (2001), 42, 4213-7215; S. Darses, G. Michaud and J-P. Genêt, Eur. J. Org. Chem., (1999), 1877-1883; M. Beavers et al., WO2005/012243; J. Org. Chem. (1994), 59, 6095-6097; A. Collier and G. Wagner, Synthetic Communications, (2006), 36; 3713-3721).

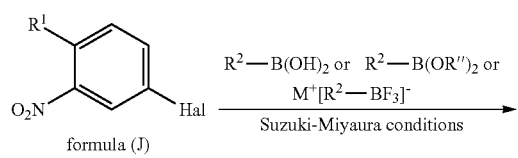

formula (J)

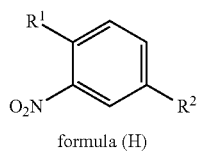

formula (H)

Compounds of formula (J) are known compounds, or may be made by known methods from known compounds (see, for example, R. Lantzsch, WO01/077062; M. Gurjar et al., Synthesis, (2000), 12, 1659; A. Kovendi and M. Kircz, Chem. Ber. (1964), 97 (7), 1896; G. Ecke et al., J. Org. Chem., (1957), 22, 639).

In an alternative approach, a compound of formula (A), wherein G is $C_1$-$C_4$ alkyl, may be prepared by treating a compound of formula (K), wherein G is $C_{1-4}$ alkyl, and Hal is a halogen such as bromide or iodide, with an arylboronic acid of formula (L) in the presence of a suitable palladium catalyst, and a base and preferably in the presence of a suitable ligand, and in a suitable solvent. Preferably the palladium catalyst is palladium acetate, the base is potassium phosphate, the ligand is 2-dicyclohexylphosphino-2′,6′-dimethoxybiphenyl and the solvent is toluene. A compound of formula (A), wherein G is H, may be prepared from a compound of formula (A), wherein G is $C_{1-4}$ alkyl, by hydrolysis, preferably in the presence of an acid catalyst such as hydrochloric acid and optionally in the presence of a suitable solvent such as tetrahydrofuran, acetone or 4-methylpentan-2-one.

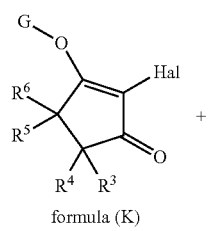

formula (K)

+

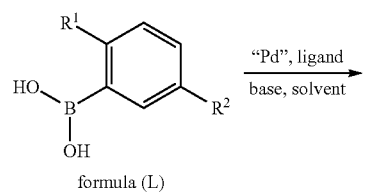

formula (L)

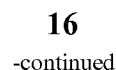

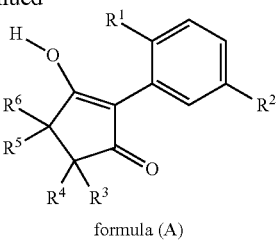

formula (A)

A compound of formula (K), wherein G is $C_{1-4}$ alkyl, may be prepared by halogenating a compound of formula (M), followed by reaction of the resulting halide of formula (N) with a $C_{1-4}$ alkyl halide or tri-$C_{1-4}$-alkylorthoformate under known conditions, for example by the procedures of R. Shepherd and A. White (J. Chem. Soc. Perkin Trans. 1 (1987), 2153) and Y.-L. Lin et al. (Bioorg. Med. Chem. 10 (2002) 685). Alternatively, a compound of formula (K) may be prepared by reacting a compound of formula (M) with a $C_{1-4}$ alkyl halide or a tri-$C_{1-4}$-alkylorthoformate, and halogenating the resulting enone of formula (O) under known conditions.

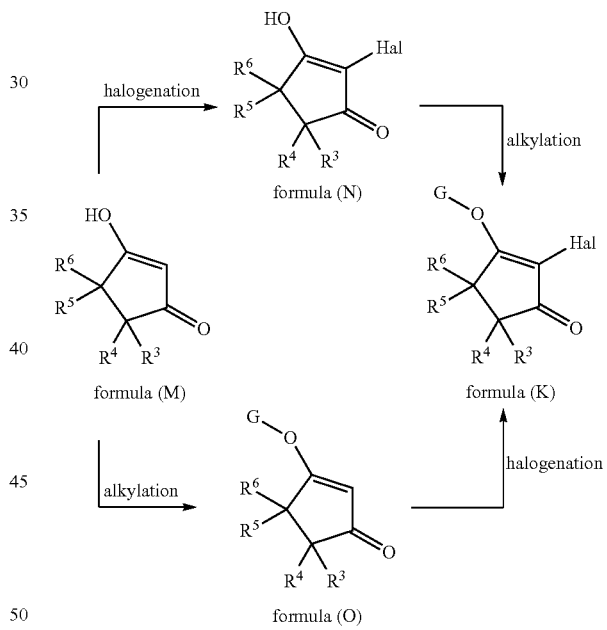

A compound of formula (L) may be prepared from an aryl halide of formula (P), wherein Hal is bromine or iodine, by known methods (see, for example, W. Thompson and J. Gaudino, J. Org. Chem., (1984), 49, 5237 and R. Hawkins et al., J. Am. Chem. Soc., (1960), 82, 3053). For example, an aryl halide of formula (P) may be treated with an alkyl lithium or alkyl magnesium halide in a suitable solvent, preferably diethyl ether or tetrahydrofuran, at a temperature of between −80° C. and 30° C., and the aryl magnesium or aryl lithium reagent obtained may then be reacted with a trialkylborate, B(OR‴)$_3$, (preferably trimethylborate or triisopropyl borate) to give an aryl dialkylboronate which may be hydrolysed to provide a boronic acid of formula (L) under acidic conditions.

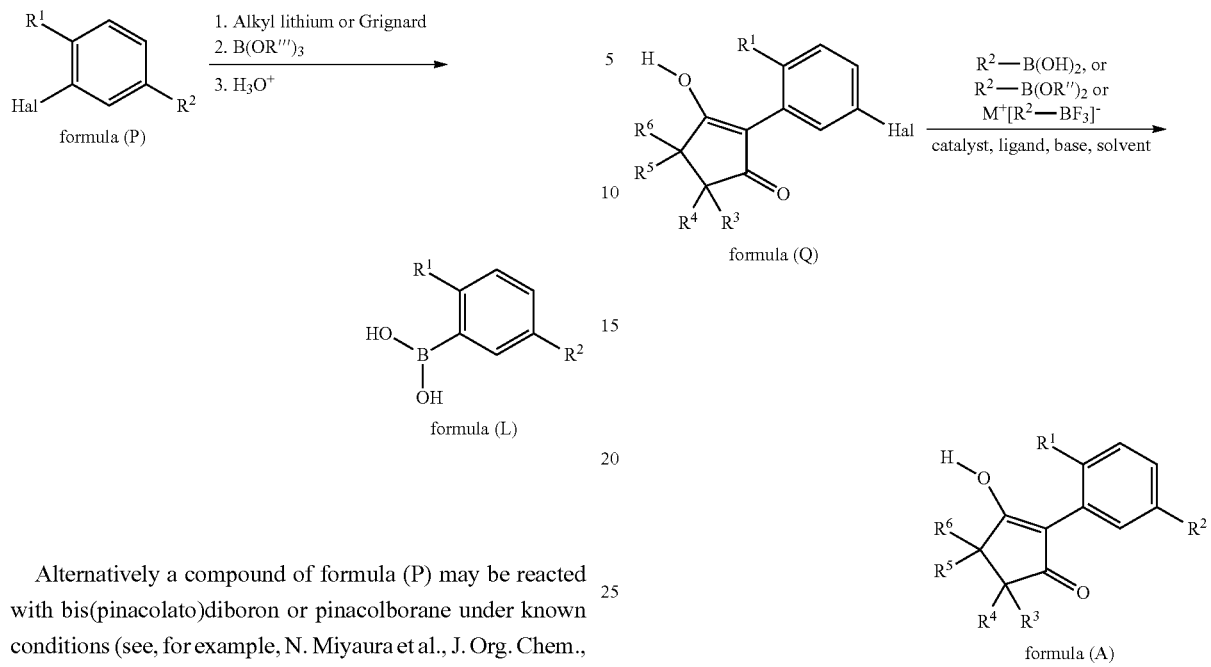

Alternatively a compound of formula (P) may be reacted with bis(pinacolato)diboron or pinacolborane under known conditions (see, for example, N. Miyaura et al., J. Org. Chem., (1995), 60, 7508, and W. Zhu and D. Ma, Org. Lett., (2006), 8 (2), 261), and in turn the resulting products may be hydrolysed under acidic conditions to give a boronic acid of formula (L).

An aryl halide of formula (P) may be prepared from an aniline of formula (G) by known methods, for example the Sandmeyer reaction, via the corresponding diazonium salts.

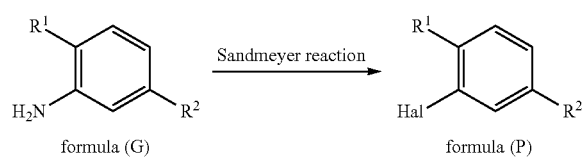

In a further approach, a compound of formula (A) may be prepared by cross-coupling an aryl halide of formula (Q), wherein Hal is chlorine, bromine or iodine, or a pseudohalide such as a trifluoromethanesulfonyl moiety, with a suitable coupling partner such as an aryl- or heteroarylboronic acid, $R^2$—$B(OH)_2$, or a suitable ester, $R^2$—$B(OR'')_2$, thereof, or a metal (especially potassium) aryl-, or heteroaryltrifluoroborate salt, $M^+[R^2$—$BF_3]^-$ in the presence of a suitable palladium catalyst, a suitable ligand and a suitable base in the presence of a suitable solvent, under Suzuki-Miyaura conditions.

Alternatively, a compound of formula (Q) may be converted into a compound of formula (A), by first converting it into an arylboronic acid, of formula (R), or a suitable salt thereof, or into a boronate ester of formula (T), followed by cross-coupling with an aryl- or heteroaryl halide, $R^2$-Hal (wherein Hal is chlorine, bromine or iodine or a pseudohalide such as a trifluoromethanesulfonyl moiety) under Suzuki-Miyaura conditions. The conversion of a compound of formula (Q) to a compound of formula (R) may be effected by treatment with at least two equivalents of a suitable metallating agent such as an alkyl lithium or an alkyl magnesium halide in a solvent such as tetrahydrofuran or diethyl ether, or by treatment with at least one equivalent of a suitable base (such as sodium hydride) followed by treatment of the resulting anion with at least one equivalent of a suitable metallating agent in a suitable solvent such as tetrahydrofuran or diethyl ether, and reacting the resulting organometallic species with a trialkylborate, $B(OR''')_3$ (preferably trimethyl borate or triisopropyl borate), to give an arylboronate of formula (S). An aryl boronate of formula (S) may be hydrolysed under acidic conditions to give an arylboronic acid of formula (R) for coupling under Suzuki-Miyaura conditions to give a compound of formula (A). Alternatively a compound of formula (Q) may be reacted with bis(pinacolato)diboron, pinacolborane or a similar reagent under known conditions (see, for example, M. Miruta et al., Synlett, (2006), 12, 1867; N. Miyaura et al., J. Org. Chem., (1995), 60, 7508, and W. Zhu and D. Ma, Org. Lett., (2006), 8 (2), 261), to give further aryl boronates of formula (T), wherein R'' is as defined previously. These arylboronates of formula (T) also may be coupled under known Suzuki-Miyaura conditions to give a compound of formula (A).

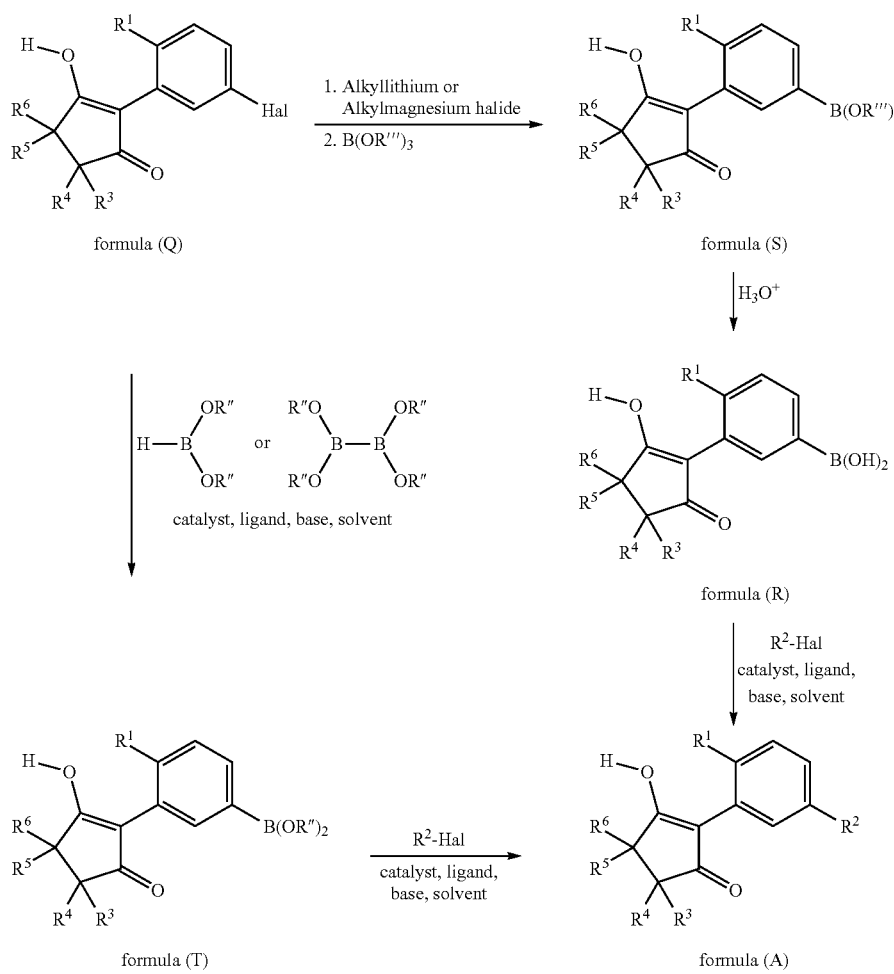

A compound of formula (Q) may be prepared from a compound of formula (M) with an aryl lead tricarboxylate, preferably an aryl lead triacetate of formula (U) in the presence of a suitable ligand (for example N,N-dimethylaminopyridine, pyridine, imidazole, bipyridine, and 1,10-phenanthroline, preferably one to ten equivalents of N,N-dimethylaminopyridine with respect to compound (M)) in a suitable solvent (for example chloroform, dichloromethane and toluene, preferably chloroform and optionally in the presence of a co-solvent such as toluene) at 25° C. to 100° C. (preferably 60-90° C.) and optionally in the presence of a suitable catalyst such as a mercury(II) salt such as mercury(II)acetate. Similar reactions are described in the literature (for example see, J. Pinhey, B. Rowe, Aust. J. Chem., (1979), 32, 1561; J. Morgan, J. Pinhey, J. Chem. Soc. Perkin Trans. 1; (1990), 3, 715).

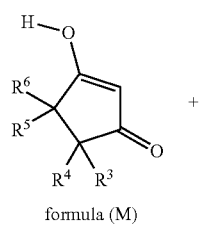

formula (M)

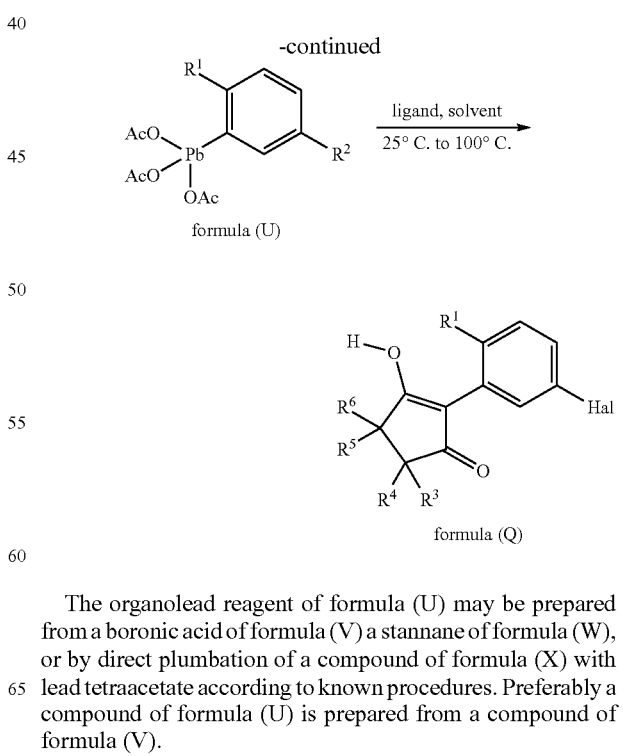

The organolead reagent of formula (U) may be prepared from a boronic acid of formula (V) a stannane of formula (W), or by direct plumbation of a compound of formula (X) with lead tetraacetate according to known procedures. Preferably a compound of formula (U) is prepared from a compound of formula (V).

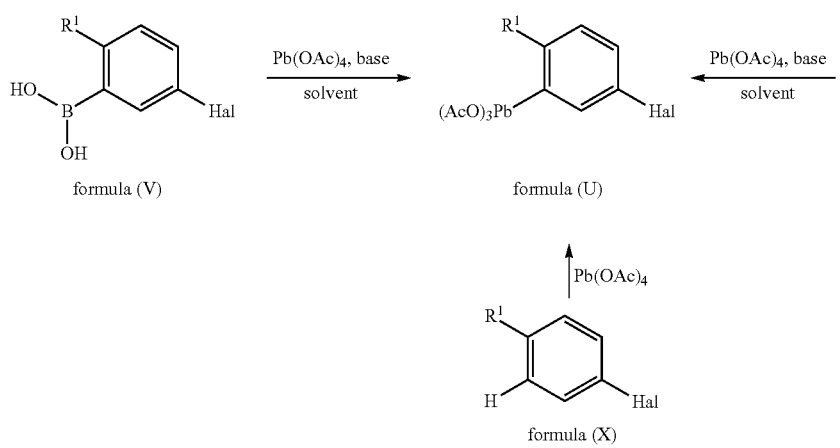

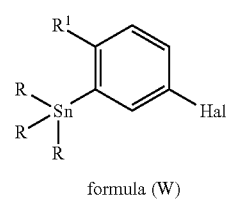

A compound of formula (V) may be prepared from an aryl iodide of formula (Y) by known methods. Boration of aryl iodides may be effected under a variety of known conditions (see, for example W. Zhu and D. Ma, Org. Lett., (2006), 6 (2), 261; M. Murata et al., Synthesis, (2007), No. 3, 351; K-T Wong et al., J. Org. Chem., (2002) 67, 1041), hydrolysis of the resulting arylborates to arylboronic acids are also known processes (see, for example, S. Coutts et al., Tetrahedron Lett., (1994), 35 (29), 5109; C. Hutton et al., Tetrahedron Lett., (2004), 45, 6657). An aryl iodide of formula (Y) may be prepared from an aniline of formula (Z), using a variety of known reaction conditions (see, for example, P. Knoche) et al., Synthesis, (2007), No. 1, 81 and references therein).

Alternatively a compound of formula (V) may be prepared from an aniline of formula (Z) by diazotisation to give an aryldiazonium salt of formula (AA), followed by boration of the resulting diazonium salt according to procedures described, for example by D. Willis and R. Strongin, (Tetrahedron Lett., (2000), 41, 8683) and hydrolysis of the resulting boronate ester to the boronic acid of formula (V) as before.

Compounds of formula (Z) are known compounds, or may be made by known methods form known compounds.

In a further approach, a compound of formula (BB), which is a compound of formula (A), wherein $R^4$ and $R^5$ are joined to form a saturated six-membered ring and R"" is hydrogen or a $C_1$-$C_2$alkyl or $C_1$-$C_2$alkoxy substituent, may be prepared from a compound of formula (CC) be reduction, for example by catalytic hydrogenation.

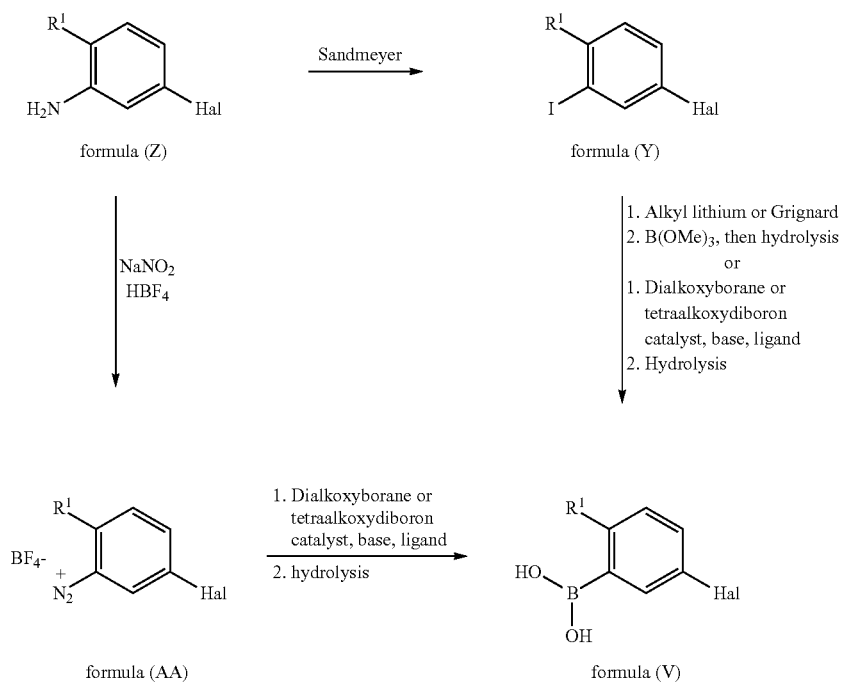

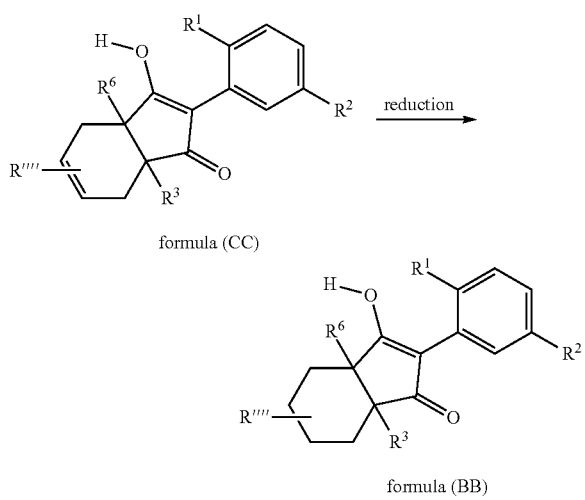

formula (CC)

formula (BB)

A compound of formula (CC) may be prepared by the reaction of a compound of formula (DD), with a compound of formula (E), optionally in the presence of a suitable solvent and a suitable catalyst.

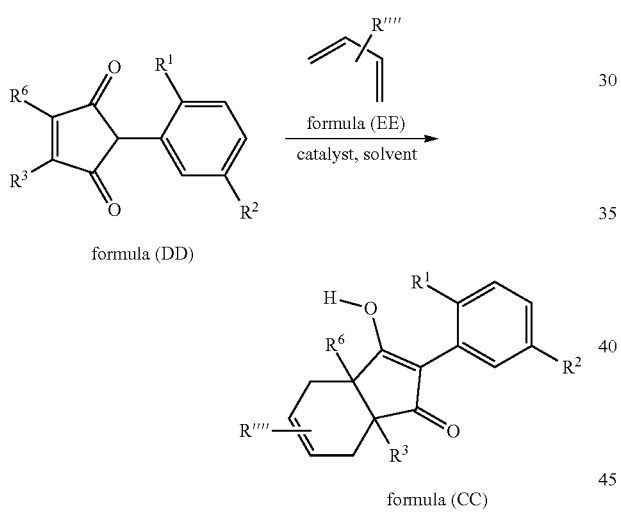

formula (DD)

formula (CC)

Preferably the catalyst is a Lewis acid catalyst such as aluminium chloride, bismuth(III)chloride, bismuth(III)trifluoromethanesulfonate, boron trifluoride, cerium(III)chloride, copper(I)trifluoromethanesulfonate, diethylaluminium chloride, hafnium(IV)chloride, iron(III)chloride, lithium perchlorate, lithium trifluoromethanesulfonate, magnesium bromide, magnesium iodide, scandium(III)trifluoromethanesulfonate, tin(IV)chloride, titanium(IV)chloride, titanium (IV)isopropoxide, trimethyl aluminium, N-trimethylsilyl-bis (trifluoromethanesulfonyl)imide, trimethylsilyl trifluoromethane-sulfonate, ytterbium(III)trifluoromethanesulfonate, zinc iodide and zirconium(IV)chloride. Magnesium iodide is particularly preferred. Suitable solvents include dichloromethane and chloroform.

Additional compounds of formula (I), wherein $R^4$ and $R^5$, together with the carbon atoms to which they are attached form a five-membered ring containing oxygen or sulfur, may be prepared by reaction of a compound of formula (DD) with carbonyl ylides or thiocarbonyl ylides. The required carbonyl ylide or thiocarbonyl ylide is normally generated in the presence of a compound of formula (DD) from known precursors by known methods (see, for example, M. Hojo et al, J. Org. Chem., (1997), 62, 8610; M. Hojo et al., Tetrahedron Lett., (1996), 37 (51), 9241; M. Hojo et al., Tetrahedron Lett., (1993), 34 (37), 5943; M. Aono et al., Tetrahedron Lett., (1986), 27 (34), 4039).

Compounds of formula (EE) are known compounds, or may be made by known methods. Those skilled in the art will realise that a compound of formula (EE) also may be generated in the presence of a compound of formula (DD) using a suitable precursor (for example by heating butadiene sulfone to approximately 110° C.) to effect conversion to a compound of formula (CC).

A compound of formula (DD), may be prepared by oxidising a compound of formula (FF) in a suitable solvent such as toluene, acetone, chloroform, dichloromethane or 1,4-dioxane. A wide range of oxidants are suitable for effecting this transformation, including inorganic oxidants such as chromium trioxide, pyridinium dichromate, manganese dioxide and aluminium alkoxides such as aluminium isopropoxide, as well as organic oxidants such as 2,3-dichloro-5,6-dicyano-p-benzoquinone and hypervalent iodine oxidants such as 1,1, 1,-tris(acetyloxy)-1,1-dihydro-1,2-benziodoxol-3-(1H)-one (Dess-Martin periodinane). Suitable procedures for effecting this oxidation are described, for example, by K. Saito and H. Yamchika, U.S. Pat. No. 4,371,711, and by G. Piancatelli et al., Tetrahedron (1978), 34 (18), 2775.

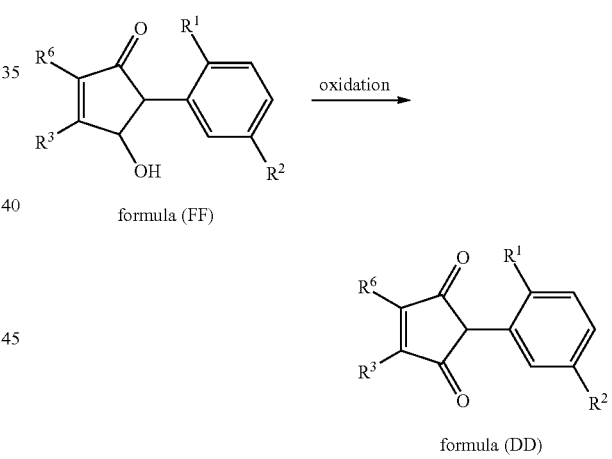

formula (FF)

formula (DD)

A compound of formula (FF) may be prepared from a compound of formula (GG) by treatment with a suitable acid catalyst in the presence of water and optionally in the presence of a suitable co-solvent.

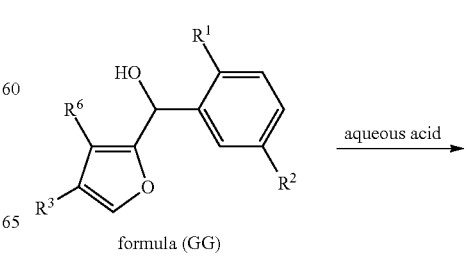

formula (GG)

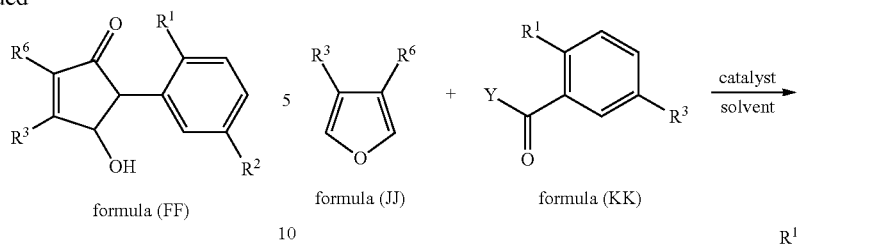

formula (FF)    formula (JJ)    formula (KK)

For example, a compound of formula (GG) may be converted to a compound of formula (FF) in the presence of an aqueous solution of an acid such as formic acid, dichloroacetic acid, trichloroacetic acid, phosphoric acid, polyphosphoric acid and pyrophosphoric acid, optionally in the presence of a co-solvent such as acetone, butanone, dioxane or tetrahydrofuran by methods similar to those described, for example, by K. Saito and H. Yamchika, U.S. Pat. No. 4,371,711. Preferably the acid is polyphosphoric acid or phosphoric acid. Alternatively a compound of formula (FF) may be prepared from a compound of formula (GG) by rearrangement in the presence of a Lewis acid catalyst such as zinc chloride in a suitable solvent such as water, optionally in the presence of a suitable co-solvent such as optionally in the presence of a co-solvent such as acetone, butanone, dioxane or tetrahydrofuran by procedures similar to that described by G. Piancatelli et al., Tetrahedron, (1978), 34 (18), 2775.

A compound of formula (GG) may be prepared by the reduction of a compound of formula (HH) by known conditions (see, for example R. Silvestri et al., J. Med. Chem., (2005), 48, 4378).

formula (HH)

Alternatively a compound of formula (GG) may be prepared by the addition of a suitable organometallic reagent such as an arylmagnesium halide of formula (LL) wherein Hal is a halide such as chloride, bromide or iodide, or an aryllithium reagent of formula (MM) or diarylzinc reagent of formula (NN) to a furan-2-carboxaldehyde of formula (OO) in a suitable solvent such as diethyl ether or tetrahydrofuran according to known procedures (see, for example G. Panda et al., Tetrahedron Lett., (2005), 46, 3097).

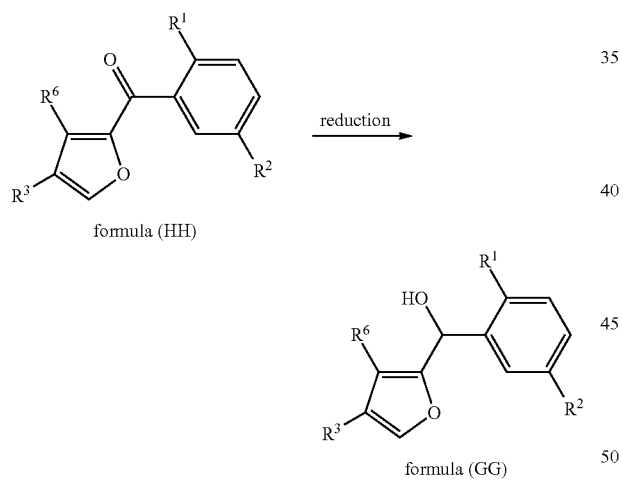

formula (HH) → reduction → formula (GG)

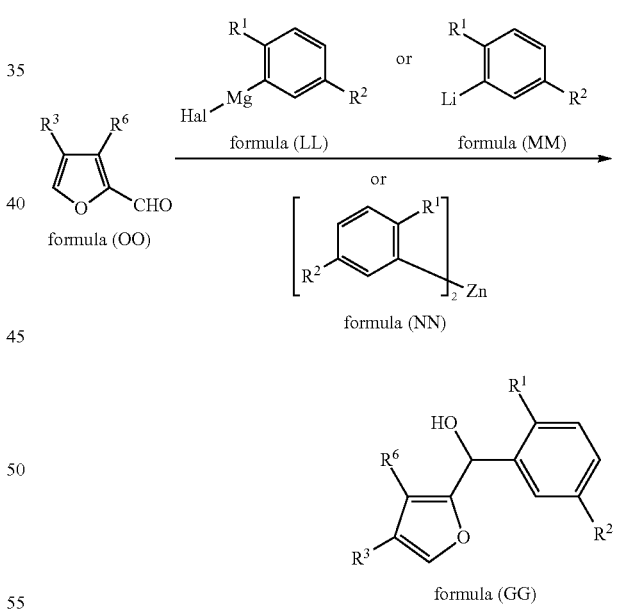

formula (OO)    formula (LL)    formula (MM)    formula (NN)    formula (GG)

Compounds of formula (HH) may be made by acylating a furan of formula (JJ) with a suitable carboxylic acid or acid chloride of formula (KK) (wherein Y is OH, or chlorine) or a similar reagent (such as a carboxylic acid anhydride, or a suitable thioester), optionally in the presence of a suitable catalyst (such as a Lewis acid catalyst such as aluminium chloride, aluminium dodecatungstophosphate, bismuth(III) trifluoromethanesulfonate, indium(III)trifluoromethanesulfonate or scandium(III)trifluoromethanesulfonate), and optionally in a suitable solvent (such as dichloromethane, chloroform, acetonitrile, nitromethane and hexane), under known conditions (see, for example, H. Firouzabadi, N. Iranpoor and F Nowrouzi, Tetrahedron, (2004), 60, 10843, R. Silvestri et al., J. Med. Chem., (2005), 48 (13), 4378 and references therein).

Additional compounds of formula (GG) may be prepared from compounds of formula (JJ) by reaction with an alkyl lithium reagent, such as n-butyllithium, optionally in the presence of an additive such as tetramethylethylenediamine, and in a suitable solvent such as diethyl ether or tetrahydrofuran, followed by reaction with a benzaldehyde of formula (PP) as described, for example by I. Gupta and M. Ravikanth, J. Org. Chem., (2004), 69, 6796; A. Echavarren et al., J. Am. Chem. Soc., (2003), 125 (19), 5757 and by T. Chandrashekar et al., J. Org. Chem., (2002), 67, 6309.

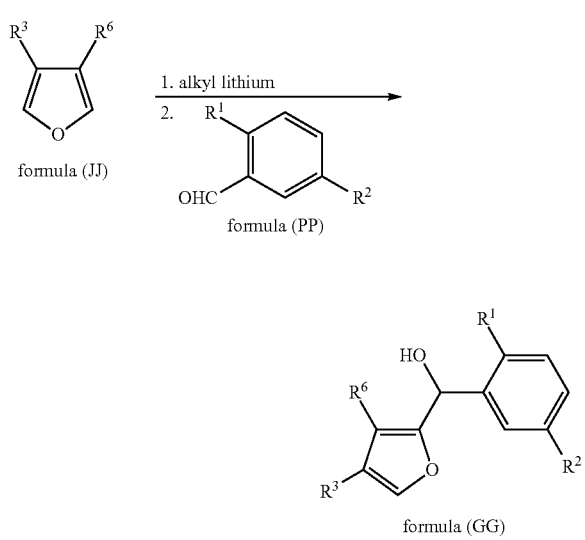

formula (JJ)

formula (PP)

formula (GG)

Compounds of formula (JJ) and formula (PP) are known, or may be made by known methods form known compounds. Compounds of formula (PP) may be prepared from compounds of formula (P) by known methods. For example, a compound of formula (P) may be treated with an alkyl lithium or alkyl magnesium halide, or with lithium or magnesium, in a suitable solvent, preferably diethyl ether or tetrahydrofuran, at a temperature of between −80° C. and 30° C., and the resulting aryl magnesium or aryl lithium species may be reacted with a suitable formylating reagent such as N,N-dimethylformamide, N-formylmorpholine, N-formylpiperidine, or a trialkyl orthoformate such as triethyl orthoformate according to known procedures (see, for example J. Einhorn and J. Luche, Tetrahedron Lett., (1986); 27 (16) 1793; G. Olah, L. Ohannesian and M. Arvanaghi, J. Org. Chem., (1984), 49 (20), 3856; D. Nelson and E. Uschak, J. Org. Chem., (1977), 42 (20), 3308; C. Dornfeld and G. Colman, Org. Synth. Coll. Vol. 3, (1955), 701; L. Smith and M. Bayliss, J. Org. Chem., (1941), 6, 437). Alternatively, a compound of formula (PP) may be prepared by reaction of a compound of formula (P) with carbon monoxide and a suitable hydrogen donor (such as poly(methylhydro-siloxane), hydrogen, formic acid or sodium formate) in the presence of a suitable catalyst (especially a palladium catalyst such as tetrakis(triphenylphosphine)palladium(0), bis(triphenylphosphine)palladium(II)dibromide, bis(triphenylphosphine)palladium(II)dichloride and palladium(II)acetate), according to known methods (see, for example, M-Z. Cai, H. Zhao, J. Zhou and C-S. Song., Synth. Commun., (2002), 32 (6), 923; T. Okano, N. Harada and J. Kiji, Bull. Chem. Soc. Jpn., (1994), 67 (8), 2329; I. Pri-Bar and O. Buchman, J. Org. Chem., (1984), 49 (21), 4009; A. Schoenberg and R. Heck., J. Am. Chem. Soc., (1974), 96 (25), 7761).

Additional compounds of formula (BB) may be made by procedures similar to those detailed above. For example, a compound of formula (BB) may be prepared by cross-coupling an aryl halide of formula (QQ), wherein Hal is chlorine or bromine, with a suitable coupling partner such as an aryl- or heteroarylboronic acid, $R^2$—$B(OH)_2$, or a suitable ester, $R^2$—$B(OR'')_2$, thereof, or a metal (especially potassium) aryl-, or heteroaryltrifluoroborate salt, $M^+[R^2$—$BF_3]^-$ in the presence of a suitable palladium catalyst, a suitable ligand and a suitable base in the presence of a suitable solvent, under Suzuki-Miyaura conditions.

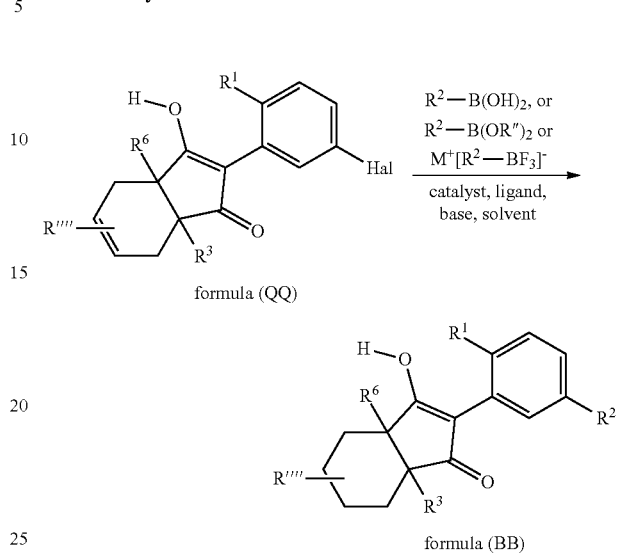

formula (QQ)

formula (BB)

A compound of formula (QQ) may be prepared from a compound of formula (RR) and a compound of formula (EE), optionally in the presence of a suitable Lewis Acid catalyst and optionally in a suitable solvent.

formula (RR)

formula (EE)

formula (QQ)

A compound of formula (RR) may be prepared by methods analogous to those used to describe the preparation of a compound of formula (DD). For example, a compound of formula (RR) may be prepared from a compound of formula (OO), by reaction with a known compound of formula (SS) or formula (TT) or formula (UU) by methods previously described for the preparation of a compound of formula (DD).

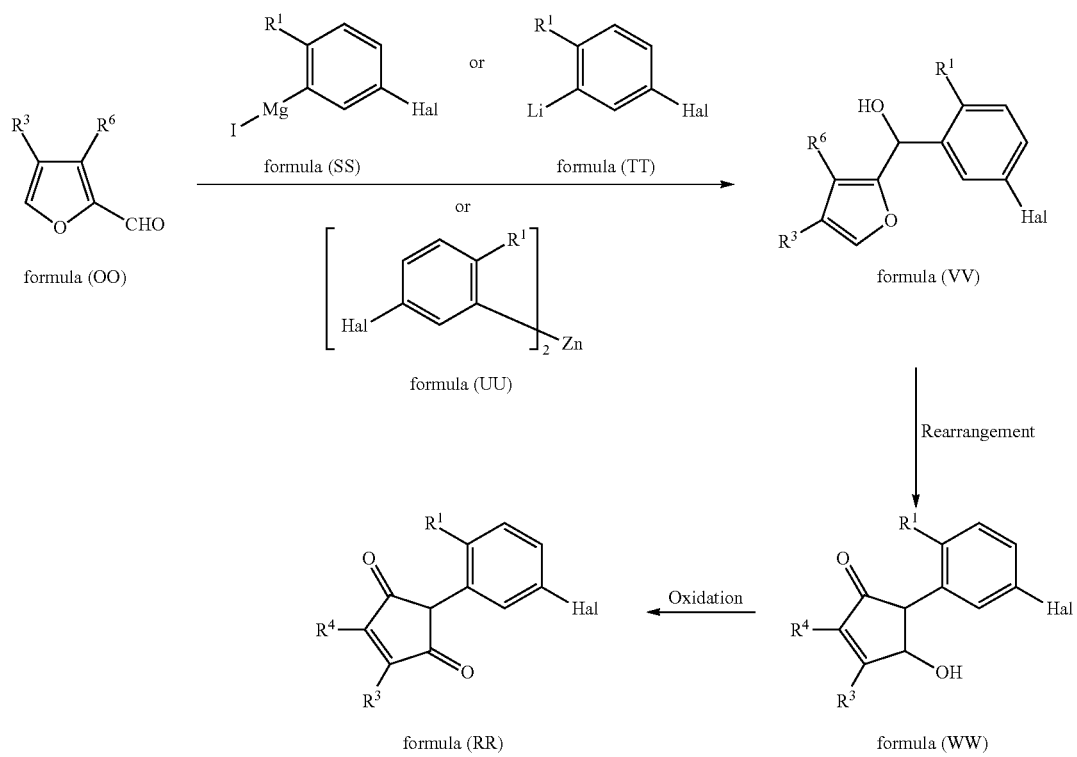

The compounds of formula I according to the invention can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyro-lactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifying, wetting or suspending agents or for other purposes. Typical surface-active substances include, for example, salts of alkyl sulfates, such as diethanolammonium lauryl sulfate; salts of alkylarylsulfonates, such as calcium dodecyl benzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further adjuvants described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides.

The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). Further oil additives that are preferred according to the invention are SCORE® (Syngenta Crop Protection Canada) and Adigor® (Syngenta Crop Protection Canada).

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pene-trate®, can also be mixed into the spray mixture as activity-enhancing agents.

The herbicidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1-2000 g/ha, preferably 1-1000 g/ha and most preferably at 1-500 g/ha.

Preferred formulations have especially the following compositions:
(%=percent by weight):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for application in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly disperse silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated under reduced pressure.

| F5. Coated granules | a) | b) | c) |
|---|---|---|---|
| active ingredient | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, and for non-selective weed control, which comprises treating the useful plants or the area under cultivation or the locus thereof with a compound of formula I.

Crops of useful plants in which the compositions according to the invention can be used include especially cereals, in particular wheat and barley, rice, corn, rape, sugarbeet, sugarcane, soybean, cotton, sunflower, peanut and plantation crops.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*. Control of monocotyledonous weeds, in particular *Agrostis, Avena, Setaria, Lolium, Echinochloa, Bromus, Alopecurus* and *Sorghum* is very extensive.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with other herbicides. The following mixtures of the compound of formula I are especially important. Preferably, in these mixtures, the compound of the formula I is one of those compounds listed in Tables 1 to 20 below:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atrazine, formula I+aviglycine, formula I+azafenidin, compound of formula I+azimsulfuron, compound of formula I+BCPC, compound of formula I+beflubutamid, compound of formula I+benazolin, formula I+bencarbazone, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, formula I+bromophenoxim, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, formula I+desmetryn, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, formula I+dipropetryn, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, formula I+ethephon, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fenoxasulfone (CAS RN 639826-16-7), compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, formula I+fluazolate, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, formula I+flumetralin, compound of formula I+flumetsulam, compound of formula I+flumiclorac, compound of formula I+flumiclorac-pentyl, compound of formula I+flumioxazin, formula I+flumipropin, compound of formula I+fluometuron, compound of formula I+fluoroglycofen, compound of formula I+fluoroglycofen-ethyl, formula I+fluoxaprop, formula I+flupoxam, formula I+flupropacil, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone (CAS RN 212201-70-2), compound of formula I+isoproturon, compound of formula I+isouron, compound of formula I+isoxaben, compound of formula I+isoxachlortole, compound of formula I+isoxaflutole, formula I+isoxapyrifop, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazosulfuron (NC-620, CAS RN 868680-84-6), compound of formula I+methabenzthiazuron, formula I+methazole, compound of formula I+methylarsonic acid, compound of formula I+methyldymron, compound of formula I+methyl isothiocyanate, compound of formula I+metobenzuron, formula I+metobromuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, formula I+NDA-402989, compound of formula I+neburon, compound of formula I+nicosulfuron, formula I+nipyraclofen, formula I+n-methyl glyphosate, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, formula I+prohexadione-calcium, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron (TH-547, CAS RN 570415-88-2), compound of formula I+propyzamide, compound of formula I+prosulfocarb, compound of formula I+prosulfuron, compound of formula I+pyraclonil, compound of formula I+pyraflufen, compound of formula I+pyraflufen-ethyl, formula I+pyrasulfotole, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, formula I+pyroxasulfone (KIN-485), formula I+pyroxulam, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, formula I+tebutam, compound of formula I+tebuthiuron, formula I+tefuryltrione, compound of formula 1+tembotrione, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazafluoron, compound of formula I+thiazopyr, compound of formula I+thifensulfuron, compound of formula I+thiencarbazone, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+trinexapac-ethyl, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-hydroxy-3-[[2-[(2-methoxyethoxy)methyl]-6-(trifluoromethyl)-3-pyridinyl]carbonyl]bicyclo[3.2.1]oct-3-en-2-one (CAS RN 352010-68-5), and compound of formula I+4-hydroxy-3-[[2-(3-methoxypropyl)-6-(difluoromethyl)-3-pyridinyl]carbonyl]bicyclo[3.2.1]oct-3-en-2-one.

The mixing partners for the compound of formula I may also be in the form of esters or salts, as mentioned e.g. in The Pesticide Manual, 12th Edition (BCPC) 2000.

The compounds of formula (I) according to the invention can also be used in combination with safeners. Preferably, in these mixtures, the compound of the formula (I) is one of those compounds listed in Tables 1 to 20 below. The following mixtures with safeners, especially, come into consideration:

compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecopropand compound of the formula I+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

The rate of application of safener relative to the herbicide is largely dependent upon the mode of application. In the case of field treatment, generally from 0.001 to 5.0 kg of safener/ha, preferably from 0.001 to 0.5 kg of safener/ha, and generally from 0.001 to 2 kg of herbicide/ha, but preferably from 0.005 to 1 kg/ha, are applied.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula I, optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10000 ppm, preferably from 100 to 1000 ppm.

The following Examples illustrate the invention further but do not limit the invention.

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown below, and in Table T1 are drawn as an arbitrary single enol tautomer, but it should be inferred that this description covers both the diketone form and any possible enols which could arise through tautomerism. Within the detailed experimental section the diketone tautomer is chosen for naming purposes, even if the predominant tautomer is the enol form.

EXAMPLE 1

Preparation of 2-(4'-chloro-4-ethylbiphen-3-yl)-1,3-cyclopentanedione

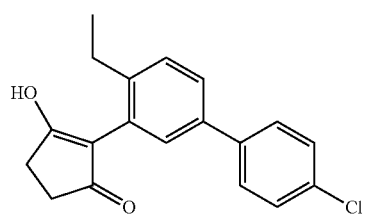 [SMILES: CCc1ccc(-c2ccc(Cl)cc2)cc1C1=C(O)CCC1=O]

Step 1: Preparation of 4-ethyl-3-nitroaniline

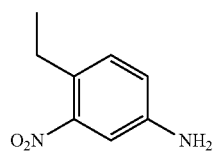

Ammonium nitrate (39.6 g, 0.49 mol) is added portionwise to a chilled (ice-bath) solution of 4-ethylaniline (20 g, 0.16 mol) in concentrated sulfuric acid (100 ml), maintaining the temperature at −10° C. to 0° C. by external cooling. The reaction mixture is stirred for two hours, then poured onto crushed ice, and the precipitate is collected by filtration. The solid is taken up in water, the solution made neutral by addition of dilute aqueous sodium hydroxide solution and extracted with ethyl acetate. The organic extracts are combined, dried over anhydrous sodium sulfate, filtered and the filtrate is evaporated in vacuo to give 4-ethyl-3-nitroaniline (20 g).

Step 2: Preparation of 4-bromo-1-ethyl-2-nitrobenzene

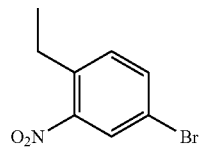

Hydrobromic acid (48% wt. in water, 240 ml) is added dropwise to a suspension of 4-ethyl-3-nitroaniline (20 g, 0.12 mol) in water (80 ml), and the mixture is stirred until the solid dissolves. The mixture is cooled to −5° C. and a solution of sodium nitrite (19.8 g, 0.28 mol) in water (100 ml) is added dropwise, maintaining the temperature at 0-5° C. Once the addition is complete, the cooling bath is removed and the reaction mixture is stirred for one hour at room temperature. The mixture is added dropwise to a pre-cooled solution of cuprous bromide (22.4 g, 0.16 mol) in hydrobromic acid (48% wt. in water) at 0° C. The reaction mixture is stirred and allowed to warm to room temperature over three hours. The mixture is extracted with diethyl ether, and the organic extracts are combined, dried over anhydrous sodium sulfate, filtered and the filtrate is concentrated in vacuo. The residue is further purified by column chromatography on silica gel, eluting with hexane to give 4-bromo-1-ethyl-2-nitrobenzene (18 g)

Step 3: Preparation of 4'-chloro-4-ethyl-3-nitrobiphenyl

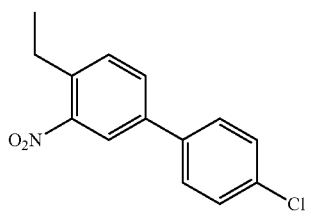 [SMILES: CCc1ccc(-c2ccc(Cl)cc2)cc1[N+](=O)[O-]]

To 4-bromo-1-ethyl-2-nitrobenzene (20.0 g, 0.087 mol) in 150 ml 1,2-dimethoxyethane is added, at room temperature, 4-chlorophenylboronic acid (14.98 g, 0.096 mol) and tetrakis(triphenylphosphine)palladium(0) (2.0 g, 0.00174 mol) and nitrogen gas is bubbled through the mixture. After stirring for 10 minutes at 20° C., a solution of sodium carbonate (73.8 g, 0.696 mol) in water (350 ml) is added and mixture is refluxed for 16 hours. The reaction mixture is cooled to room temperature, filtered through diatomaceous earth, washing with 200 ml of ethyl acetate. The mixture is poured into a separating funnel and the two phases are separated. The aqueous phase is extracted with ethyl acetate. The organic extracts are combined, dried over anhydrous magnesium sulfate, filtered and the filtrate is evaporated in vacuo to give 4'-chloro-4-ethyl-3-nitrobiphenyl (23.84 g) as a brown oil used without further purification in the next step.

Step 4: Preparation of
3-amino-4'-chloro-4-ethylbiphenyl

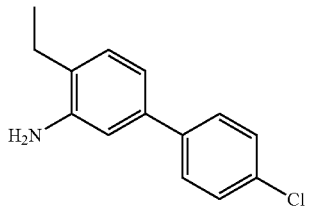

4'-Chloro-4-ethyl-3-nitrobiphenyl (22.6 g, 0.086 mol) is suspended in methanol (250 ml) and the reaction mixture is stirred at room temperature. Distilled water (100 ml) is added, followed by zinc dust (39.0 g, 0.60 mol) and ammonium chloride (13.8 g, 0.26 mol) and the mixture is heated to reflux for 1 hour. The reaction mixture is cooled to room temperature, filtered through diatomaceous earth and the filtrate is evaporated in vacuo to remove most of the methanol. The residue is partitioned between ethyl acetate (200 ml) and water and the aqueous phase is re-extracted with ethyl acetate (200 ml). The organic extracts are combined, washed with water and brine, dried over anhydrous magnesium sulfate, filtered and the filtrate is evaporated in vacuo to give 3-amino-4'-chloro-4-ethylbiphenyl (15.0 g) as a colourless solid. The product is used directly without further purification in Step 5.

Step 5: Preparation of
3-bromo-4'-chloro-4-ethylbiphenyl

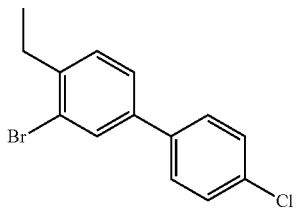 [SMILES: CCc1ccc(-c2ccc(Cl)cc2)cc1Br]

Step 5a

3-Amino-4'-chloro-4-ethylbiphenyl (60.0 g, 0.26 mol) is added portionwise to a mixture of hydrobromic acid (48% wt. in water, 350 ml) and water (250 ml), and once the addition is complete the mixture is heated to 40° C. and stirred for 20 minutes, before being cooled to 5° C. in an ice bath. A solution of sodium nitrite (20.65 g, 0.30 mol) in water (100 ml) is added dropwise over 45 minutes, and once the addition is complete the mixture is stirred at 5° C. for a further 45 minutes.

Step 5b

Meanwhile, hydrobromic acid (48% wt. in water, 400 ml) is heated and stirred at 70° C. and copper sulfate pentahydrate (74.75 g, 0.30 mol) is added in one portion and the mixture is stirred at 70° C. for two minutes to give a dark purple solution, and then copper powder (26.44 g, 0.42 mol) is added in one portion, resulting in a pink suspension.

Step 5c

The mixture containing the diazonium salt (prepared in step 5a) is added portionwise over 70 minutes to the stirred mixture prepared in Step 5b at 70° C. (in between additions the mixture containing the diazonium salt is kept cold in an ice bath). Once the addition is complete the mixture is stirred at 70° C. for a further 30 minutes and then allowed to cool to room temperature, and extracted with ethyl acetate (3×500 ml). The organic extracts are combined, washed with water and brine, dried over anhydrous magnesium sulfate, filtered and the filtrate is evaporated in vacuo. Purification by column chromatography on silica gel affords 3-bromo-4'-chloro-4-ethylbiphenyl (52.1 g) as a yellow oil Step 6: Preparation of
4'-chloro-4-ethylbiphen-3-ylboronic acid

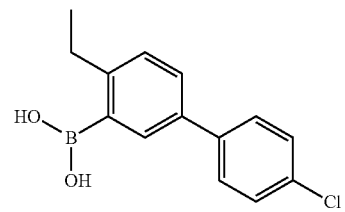 [SMILES: CCc1ccc(-c2ccc(Cl)cc2)cc1B(O)O]

3-Bromo-4'-chloro-4-ethylbiphenyl (10 g, 0.03 mol) is dissolved in tetrahydrofuran (250 ml), and the temperature is cooled to −78° C. n-Butyllithium (1.33 molar solution in hexanes, 34.6 ml,) is added dropwise over 30 minutes, maintaining the temperature at around −78° C. The reaction mixture is stirred for one and a half hours, then trimethylborate (4.9 g, 0.05 mol) is added dropwise and the reaction mixture is stirred for two hours. A solution of 2N aqueous hydrochloric acid (100 ml) is added dropwise, and once the addition is complete the mixture is stirred for two hours. The mixture is concentrated to remove most of the tetrahydrofuran, then diluted with water and extracted with diethyl ether. The organic extracts are washed with water and brine, combined, dried over anhydrous sodium sulfate, filtered and the filtrate is evaporated in vacuo. The residue is further purified by flash column chromatography on silica gel, eluting with 7% ethyl acetate in hexane to give 4'-chloro-4-ethylbiphen-3-ylboronic acid (5.4 g).

Step 7: Preparation of
2-bromo-3-methoxycyclopent-2-enone

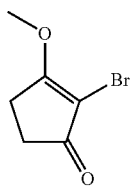

N-Bromosuccinimide (24.92 g, 0.140 mol) is added, portionwise over one hour, to a stirred solution of 3-methoxycyclopent-2-enone (14.95 g, 0.133 mol) in 1,2-dichloroethane (300 ml) at 0° C. in an amber flask. The reaction is stirred at 0° C. for a further 90 minutes and then any remaining solid is removed by filtration. The filtrate is evaporated under reduced pressure, and the residue is dissolved in warm toluene (600 ml) and washed quickly with ice-cold water (2×100 ml). The organic phase is dried over anhydrous magnesium sulfate, filtered and the filtrate is evaporated under reduced pressure until approximately 150 ml remains. The flask is cooled in an ice bath and left for 30 minutes. The resultant precipitate is removed by filtration, washed with hexane (50 ml) and dried to give 2-bromo-3-methoxycyclopent-2-enone (17.5 g, 69%).

Step 8: Preparation of 2-(4'-chloro-4-ethylbiphen-3-yl)-3-methoxycyclopent-2-enone

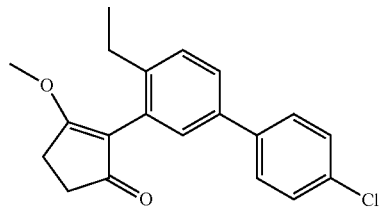 [SMILES: CCc1ccc(-c2ccc(Cl)cc2)cc1C1=C(OC)CCC1=O]

To a stirred suspension of 2-bromo-3-methoxycyclopent-2-enone (1.0 g, 5.23 mmol), 4'-chloro-4-ethylbiphen-3-ylboronic acid (2.03 g, 7.80 mmol) and potassium phosphate (2.23 g, 10.50 mmol) in anhydrous, degassed toluene (25 ml) under an atmosphere of nitrogen is added palladium(II)acetate (24 mg, 0.105 mmol) and 2-dicyclohexylphosphino-2',6'-dimethoxybiphenyl (86 mg, 0.209 mmol). The reaction is heated at 90° C. for 4 hours and then allowed to cool to room temperature, quenched with water (40 ml) and extracted with ethyl acetate (3×30 ml). The organic extracts are combined, washed with brine (15 ml), dried over anhydrous magnesium sulfate, filtered and the filtrate is evaporated under reduced pressure. The residue is purified by column chromatography on silica gel to give 2-(4'-chloro-4-ethylbiphen-3-yl)-3-methoxycyclopent-2-enone (1.29 g, 75%).

Step 9: Preparation of 2-(4'-chloro-4-ethylbiphen-3-yl)-1,3-cyclopentanedione

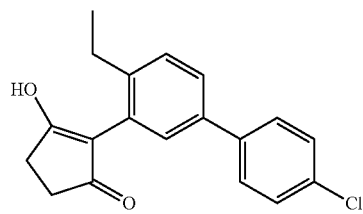 [SMILES: CCc1ccc(-c2ccc(Cl)cc2)cc1C1=C(O)CCC1=O]

A solution of 2-(4'-chloro-4-ethylbiphen-3-yl)-3-methoxycyclopent-2-enone (200 mg, 0.61 mmol) in acetone (4 ml) and 2M aqueous hydrochloric acid (4 ml) is heated at 120° C. for 20 minutes under microwave irradiation. The reaction mixture is diluted with water (20 ml) and 2M aqueous hydrochloric acid (10 ml), and the crude product is extracted with ethyl acetate (3×15 ml). The organic extracts are combined, washed with brine (10 ml), dried over anhydrous magnesium sulfate, filtered and the filtrate is evaporated to dryness under reduced pressure to give 2-(4'-chloro-4-ethylbiphen-3-yl)-1,3-cyclopentanedione.

EXAMPLE 2

Preparation of 5-(4'-Chloro-4-ethylbiphenyl-3-yl)-tetrahydrocyclopenta[c]thiophene-4,6-dione

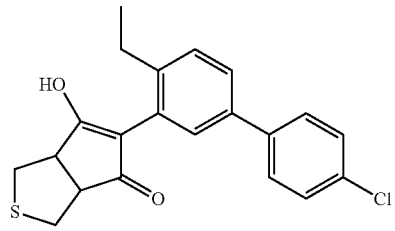 [SMILES: CCc1ccc(-c2ccc(Cl)cc2)cc1C1=C(O)C2CSCC2C1=O]

Step 1: Preparation of (4'-chloro-4-ethylbiphen-3-yl) furan-2-ylmethanol

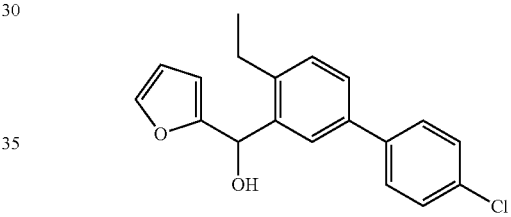

Approximately 10 ml of a solution of 3-bromo-4'-chloro-4-ethylbiphenyl (40.0 g, 135.3 mmol) in tetrahydrofuran (200 ml) is added to magnesium turnings in a dry flask, followed by a crystal of iodine. The mixture is allowed to stand without stirring for 30 minutes, then stirred once and warmed until the orange coloured mixture becomes colourless. The remainder of the 3-bromo-4'-chloro-4-ethylbiphenyl solution is added dropwise over 30 minutes with external heating applied as necessary to maintain a gentle reflux. Once the addition is complete, the mixture is heated to reflux for 2-3 hours, until only trace residues of magnesium remain. The mixture is cooled to room temperature, and then cooled further in an ice-bath. A solution of 2-furaldehyde (13.05 g, 135.8 mmol) in tetrahydrofuran (80 ml) is added dropwise over 35 minutes, and the mixture is stirred at room temperature overnight.

A second batch of material is prepared in the same way, using identical quantities of reagents and solvents, before the two batches are treated according to the procedure below.

A solution of saturated aqueous ammonium chloride (500 ml) is added to each of the mixtures prepared above, the mixtures are combined, stirred vigorously, and then allowed to stand. The two phases are separated, and the aqueous phase is extracted with ethyl acetate. The organic extracts are combined, washed with brine, dried over anhydrous magnesium sulfate, filtered and the filtrate is evaporated under reduced pressure. The residue is purified by column chromatography on silica gel to give (4'-chloro-4-ethylbiphen-3-yl)furan-2-ylmethanol (67.18 g) as a yellow oil.

Step 2: Preparation of 5-(4'-chloro-4-ethylbiphen-3-yl)-4-hydroxycyclopent-2-enone

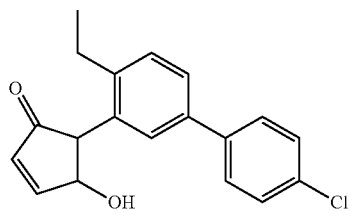 [SMILES: CCc1ccc(-c2ccc(Cl)cc2)cc1C1C(=O)C=CC1O]

A solution of (4'-chloro-4-ethylbiphen-3-yl)furan-2-ylmethanol (67.18 g, 214.8 mmol) in acetone (1340 ml) and water (235 ml) is heated to 55° C. and 30 drops of polyphosphoric acid are added. The mixture is stirred at 55° C. for 25 hours, then cooled to room temperature. The reaction mixture is concentrated under reduced pressure to remove most of the acetone then ethyl acetate (600 ml) is added, and the reaction mixture is partitioned. The aqueous phase is extracted into ethyl acetate and the organic solutions are combined, washed with saturated aqueous sodium bicarbonate solution and brine, dried over anhydrous magnesium sulfate, filtered and the filtrate is concentrated under reduced pressure. The residue is purified by column chromatography on silica gel to give 5-(4'-chloro-4-ethylbiphen-3-yl)-4-hydroxy-cyclopent-2-enone (59.84 g) as a brown oil.

Step 3: Preparation of 2-(4'-chloro-4-ethylbiphen-3-yl)cyclopent-4-ene-1,3-dione

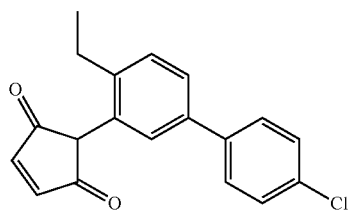 [SMILES: CCc1ccc(-c2ccc(Cl)cc2)cc1C1C(=O)C=CC1=O]

A 1.67 molar solution of Jones' reagent is prepared by adding chromium trioxide (72 g, 720 mmol) to an ice-cold mixture of concentrated sulphuric acid (72 ml) and water (360 ml) and stirring until dissolution is complete.

Jones' reagent (126 ml of 1.67 M solution, 210.4 mmol) prepared according to the procedure described above, is added dropwise over 30 minutes to a cooled (ice-bath) solution of 5-(4'-chloro-4-ethylbiphen-3-yl)-4-hydroxycyclopent-2-enone (59.84 g, 191.3 mmol) in acetone (615 ml). The mixture is stirred for 20 minutes, then the cooling bath is removed and the mixture is stirred for 1 hour at room temperature. Isopropanol (500 ml) is added to the yellow slurry and the mixture is stirred at room temperature for 2 hours. The mixture is diluted with ethyl acetate and washed with brine, dried over anhydrous magnesium sulfate, filtered and the filtrate is evaporated under reduced pressure to give 2-(4'-chloro-4-ethylbiphen-3-yl)cyclopent-4-ene-1,3-dione (47.94 g) as a yellow solid.

Step 4: Preparation of 5-(4'-chloro-4-ethylbiphenyl-3-yl)-tetrahydrocyclopenta[c]thiophene-4,6-dione

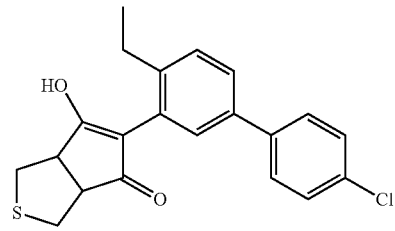 [SMILES: CCc1ccc(-c2ccc(Cl)cc2)cc1C1=C(O)C2CSCC2C1=O]

Step 4a

To a solution of bis(trimethylsilylmethyl)sulphide (1.0 g, 4.6 mmol) in dichloromethane (2 ml) at −78° C. is added a second solution of meta-chloroperbenzoic acid (0.79 g, 4.6 mmol) in dichloromethane (8 ml) dropwise, and the mixture is then stirred overnight. Additional dichloromethane is added and the organic phase is washed with ice cold saturated sodium hydrogen carbonate solution then ice cold brine. The organic phase is dried over magnesium sulfate, filtered and the filtrate is concentrated under reduced pressure to afford a mixture of bis(trimethylsilylmethyl)sulphoxide and bis(trimethylsilylmethyl)sulphide.

Step 4b

A suspension of 2-(4'-chloro-4-ethylbiphen-3-yl)cyclopent-4-ene-1,3-dione (0.200 g, 0.65 mmol) and crude bis(trimethylsilylmethyl)sulphoxide (0.406 g, 0.97 mmol) in 1,3-dimethyl-3,4,5,6-tetrahydro-2(1H)-pyrimidinone (3 ml) is heated at 100° C. for 20 minutes under microwave irradiation. The reaction mixture is then partitioned between diethylether and distilled water, and the organic phase is washed with water (×2) then brine. After drying over magnesium sulfate the crude mixture is filtered and the filtrate is concentrated under reduced pressure. The residue is purified by preparative reverse phase HPLC to afford 5-(4'-chloro-4-ethylbiphenyl-3-yl)-tetrahydrocyclopenta[c]thiophene-4,6-dione.

EXAMPLE 3

Preparation of 2-(4'-chloro-4-ethyl-2'-fluorobiphenyl-3-yl)cyclopentane-1,3-dione

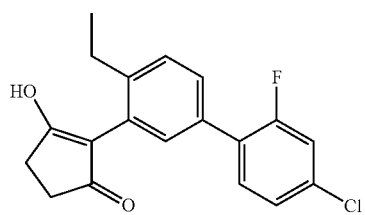

Step 1: Preparation of 4'-chloro-4-ethyl-2'-fluorobiphenyllead triacetate

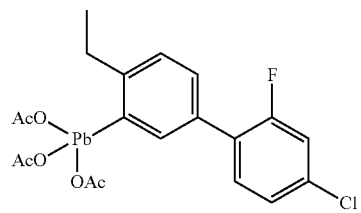

To a mixture of lead tetraacetate (29.9 g, 67 mmol) and mercuric diacetate (0.86 g, 2.7 mmol) under a nitrogen atmosphere is added anhydrous chloroform (100 ml), followed by warming to 40° C. To this solution is then added 4'-chloro-4-ethyl-2'-fluorobiphenylboronic acid (15 g, 54 mmol) and the reaction mixture is heated at 40° C. for 4 hours. After cooling to room temperature the mixture is concentrated under reduced pressure and the crude product is triturated with iso-hexane to afford 4'-chloro-4-ethyl-2'-fluorobiphenyllead triacetate as a cream solid.

Step 2: Preparation of 2-(4'-chloro-4-ethyl-2'-fluorobiphenyl-3-yl)cyclopentane-1,3-dione

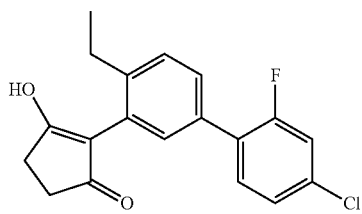 [SMILES: CCc1ccc(-c2ccc(Cl)cc2F)cc1C1=C(O)CCC1=O]

To a solution of 4'-chloro-4-ethyl-2'-fluorobiphenyllead triacetate (2.23 g, 4.6 mmol) in chloroform (30 ml) is added cyclopentanedione (0.30 g, 3.1 mmol) and 4-dimethylaminopyridine (2.61 g, 21 mmol). After stirring at room temperature for 10 minutes anhydrous toluene (6 ml) is added and the reaction mixture is heated at 80° C. for 3 hours. After cooling to room temperature the mixture is allowed to stand for 18 hours, then is diluted with dichloromethane and 2M hydrochloric acid. After filtration of the biphasic mixture through diatomaceous earth (additional washing with dichloromethane) the phases are separated and the aqueous phase is extracted again with dichloromethane (×4). The combined organic extracts are washed with brine, dried over magnesium sulfate, filtered, and the filtrate is concentrated under reduced pressure. The residue is purified by flash column chromatography (mixture of iso-hexane and ethyl acetate as eluant) to afford 2-(4'-chloro-4-ethyl-2'-fluorobiphenyl-3-yl)cyclopentane-1,3-dione.

EXAMPLE 4

Preparation of 2-(2',4'-dichloro-4-trifluoromethoxybiphenyl-3-yl)cyclopentane-1,3-dione

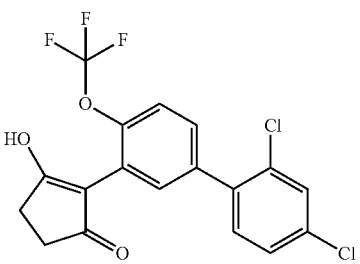 [SMILES: O=C1CCC(O)=C1c1cc(-c2ccc(Cl)cc2Cl)ccc1OC(F)(F)F]

Step 1: Preparation of 2-(5-bromo-2-trifluoromethoxyphenyl)cyclopentane-1,3-dione

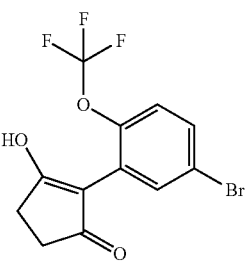 [SMILES: O=C1CCC(O)=C1c1cc(Br)ccc1OC(F)(F)F]

To a solution of 5-bromo-2-trifluoromethoxybenzaldehyde (2.0 g, 7.43 mmol) in anhydrous dichloromethane (40 ml) at room temperature is added boron trifluoride etherate (1.13 ml, 8.92 mmol) then 1,2-bis(trimethylsiloxy)cyclobutene (2.86 ml, 11.2 mmol). The mixture is stirred at room temperature for 23 hours, followed by addition of distilled water (1.2 ml) and additional boron trifluoride etherate (14.1 ml, 112 mmol). After stirring for 24 hours at room temperature the reaction mixture is then quenched with saturated aqueous ammonium chloride solution (50 ml) and extracted with dichloromethane (2×50 ml). The crude product is extracted from the organic phase by washing with 0.5 M aqueous potassium carbonate solution (×3), then acidified to pH 1 with concentrated hydrochloric acid. Final extraction with dichloromethane (×3) is followed by washing with brine then drying over magnesium sulfate and filtration. Concentration in vacuo gives a crude product which is purified by preparative reverse phase HPLC to afford 2-(5-bromo-2-trifluoromethoxyphenyl)cyclopentane-1,3-dione.

Step 2: Preparation of 2-(2',4'-dichloro-4-trifluoromethoxybiphenyl-3-yl)cyclopentane-1,3-dione

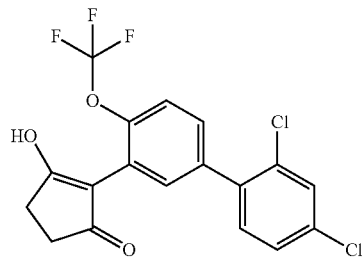 [SMILES: O=C1CCC(O)=C1c1cc(-c2ccc(Cl)cc2Cl)ccc1OC(F)(F)F]

To a mixture of 2,4-dichlorophenylboronic acid (0.075 g, 0.39 mmol), [1,1'-bis(diphenylphosphino)-ferrocene]palladium(II)chloride (0.023 g, 0.03 mmol) and cesium fluoride (0.128 g, 0.85 mM) is added a solution of 2-(5-bromo-2-trifluoromethoxyphenyl)-cyclopentane-1,3-dione (0.095 g, 0.28 mM) in degassed dimethoxyethane (1.5 mL). The mixture is purged with nitrogen, then heated at 160° C. under microwave irradiation for 15 minutes. Distilled water and ethyl acetate are added and the aqueous phase is extracted with further ethyl acetate (×2). The combined organic extracts are washed with brine, dried over magnesium sulfate, filtered and the filtrate is concentrated under reduced pressure. The residue is purified by flash column chromatography (mixture of iso-hexane and ethyl acetate as eluant) to afford 2-(2'-4'-dichloro-4-trifluoromethoxybiphenyl-3-yl)-cyclopentane-1,3-dione.

EXAMPLE 5

Preparation of 2-(2',4'-dichloro-4-cyclopropylbiphenyl-3-yl)-cyclopentane-1,3-dione

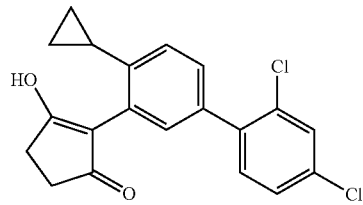

Step 1: Preparation of 5-bromo-2-cyclopropylnitrobenzene

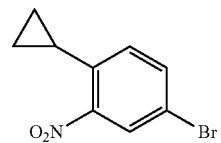 [SMILES: O=[N+]([O-])c1cc(Br)ccc1C1CC1]

To a mixture of 4-bromo-1-iodo-2-nitrobenzene (21.1 g, 0.064 mol) (described in Synthesis, (2008), (13), 2039-2044), cyclopropyl boronic acid (7.2 g, 0.083 mol), tricyclohexyl phosphine (1.7 g, 0.0064 mol) and potassium phosphate (50.0 g, 0.24 mol) is added toluene (255 ml) and distilled water (23 ml). The stirred mixture is degassed then flushed with nitrogen (cycle repeated×3), followed by addition of palladium(II) acetate (0.70 g, 0.0032 mol) and heating at 100° C. overnight. After cooling to room temperature the mixture is quenched with distilled water and extracted with ethyl acetate (×3). All organics fractions are combined, washed with distilled water then brine, and dried over magnesium sulfate. Concentration in vacuo affords an approximate 6:4 mixture of 5-bromo-2-cyclopropylnitrobenzene and 4-bromo-1-iodo-2-nitrobenzene (11.9 g) as a brown oil. To this crude mixture is then added additional cyclopropyl boronic acid (1.8 g, 0.021 mol), tricyclohexylphosphine (0.43 g, 0.0016 mol), palladium acetate (0.18 g, 0.0008 mol), potassium phosphate (12.5 g, 0.06 mol), toluene (65 ml) and water (6 ml). After heating at 100° C. overnight the suspension is allowed to cool to room temperature and the mixture is quenched with distilled water and extracted with ethyl acetate (×3). All organics fractions are combined, washed with distilled water then brine, and dried over magnesium sulfate. Concentration in vacuo affords a crude product which is purified by flash column chromatography on silica gel to give a mixture of 5-bromo-2-cyclopropylnitrobenzene, 3-bromo-nitrobenzene and 2,5-dicyclopropyl-nitrobenzene which is used in the next step without further purification.

Step 2: Preparation of 5-bromo-2-cyclopropylaniline

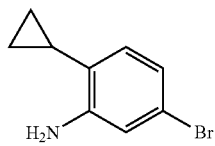

Tin(II)chloride (16.0 g, 0.10 mol) is added in one portion to a solution of crude 5-bromo-2-cyclopropylnitrobenzene (8.68 g) in ethanol (190 ml) and water (1.9 ml). The reaction mixture is stirred at room temperature overnight, followed by addition of further tin(II)chloride (28 g, 0.175 mol) and additional stirring overnight. After concentration in vacuo ice is added, and the solution is basified with 2M aqueous sodium hydroxide. After extraction with ethyl acetate (×2) the organic phase is washed again with 2M aqueous sodium hydroxide, then also distilled water and brine. After drying over magnesium sulfate the solution is concentrated in vacuo to give a brown oil which is purified by flash column chromatography on silica gel (9:1 isohexane/ethyl acetate eluant) to afford 5-bromo-2-cyclopropylaniline as a brown oil.

Step 4: Preparation of 5-bromo-2-cyclopropyliodobenzene

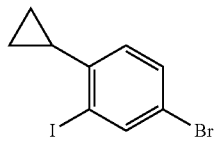 [SMILES: Brc1ccc(C2CC2)c(I)c1]

5-Bromo-2-cyclopropylaniline (4.74 g) is added to a solution of para-toluene sulfonic acid monohydrate (12.2 g, 0.064 mol) in acetonitrile (130 ml), followed by stirring for 10 minutes at room temperature. The suspension is then cooled to 10° C. and a mixed solution of sodium nitrite (8.9 g, 0.054 mol) and potassium iodide (3.1 g, 0.044 mol) in water (16 ml) is added dropwise over 30 minutes. Once the addition is complete the reaction mixture is allowed to stir at 10° C. for 20 minutes and then at room temperature for 4 hours. The reaction mixture is basified to pH 9-10 with aqueous sodium bicarbonate, followed by addition of ethyl acetate and 10% aqueous sodium metabisulphite. The phases are separated and the aqueous layer is extracted again with ethyl acetate (×2). Organics are combined, washed with brine, dried over magnesium sulfate then concentrated in vacuo to give the crude product which is purified by flash column chromatography on silica gel (isohexane eluant) to afford 5-bromo-2-cyclopropyliodobenzene as a colourless oil.

Step 5: Preparation of 5-bromo-2-cyclopropylphenyl boronic acid

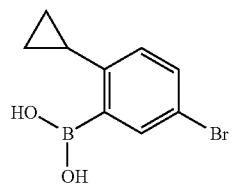 [SMILES: OB(O)c1cc(Br)ccc1C1CC1]

To a solution of 5-bromo-2-cyclopropyliodobenzene (5.67 g, 0.018 mol) in anhydrous tetrahydrofuran (32 ml) at −78° C. is added isopropylmagnesium chloride (9.5 ml, 0.019 mol, 2M solution in THF) at such a rate as to maintain a temperature below −60° C. Once addition is complete the reaction mixture is stirred for 20 minutes at this temperature and then allowed to warm to room temperature and stir for an additional 2 hours. The solution is then cooled again to −78° C. and triisopropylborate (8.3 ml, 0.036 mol) is added dropwise. After stirring at this temperature for 10 minutes the solution is allowed to warm to room temperature and stir for an additional 2 hours. After quenching with 2M aqueous hydrochloric acid (20 ml) the reaction mixture is diluted with distilled water then extracted with ethyl acetate (×3). Organic fractions are combined, washed with distilled water and brine, then dried over magnesium sulfate and concentrated in vacuo. The crude solid is azeotroped with toluene (×3) then triturated with isohexane to afford 5-bromo-2-cyclopropylphenyl boronic acid as a cream solid.

Step 6: 5-bromo-2-cyclopropylphenyl lead triacetate

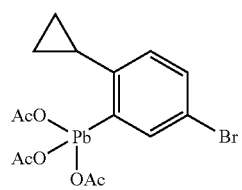

To a solution of lead(IV)acetate (4.0 g, 0.0089 mol) and mercury(II)acetate (139 mg, 0.45 mmol) in chloroform (12 ml) at 50° C. is added 5-bromo-2-cyclopropylphenyl boronic acid (2.0 g, 0.0083 mol), and the solution is heated at this temperature for 5 hours. After cooling to room temperature the suspension is further cooled to 0° C. and anhydrous potassium carbonate (1.8 g) is added with rapid stirring for 2 minutes. The reaction mixture is then filtered (washing with additional chloroform), and the filtrate is concentrated to half its original volume and the crude product is precipitated with hexanes. Further concentration then filtration affords 5-bromo-2-cyclopropylphenyl lead triacetate as a beige solid.

Step 7: Preparation of 2-(5-Bromo-2-cyclopropylphenyl)cyclopentane-1,3-dione

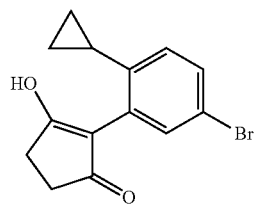 [SMILES: O=C1CCC(O)=C1c1cc(Br)ccc1C1CC1]

To a solution of cyclopentane-1,3-dione (0.57 g, 0.0058 mol) and 4-dimethylaminopyridine (3.64 g, 0.030 mol) in chloroform (33 ml) is added toluene (9 ml) then 5-bromo-2-cyclopropylphenyl lead triacetate (3.77 g, 0.0065 mol). This solution is heated at 80° C. for 20 hours then cooled to room temperature and diluted with dichloromethane and 2M aqueous hydrochloric acid. The resulting biphasic suspension is filtered through diatomaceous earth and the two phases are separated. The organic layer is further washed with 2M aqueous hydrochloric acid and the aqueous phase is extracted again with dichloromethane. All organic fractions are combined, washed with brine, dried over magnesium sulfate then concentrated in vacuo. The crude product is finally purified by flash column chromatography on silica gel (isohexane/ethyl acetate eluant) to afford 2-(5-bromo-2-cyclopropylphenyl)cyclopentane-1,3-dione as a pale yellow solid.

Step 8: Preparation of 2-(2',4'-dichloro-4-cyclopropylbiphenyl-3-yl)-cyclopentane-1,3-dione

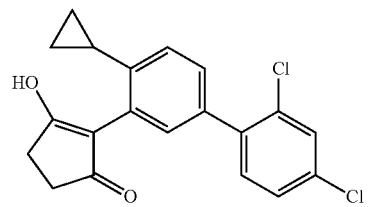 [SMILES: O=C1CCC(O)=C1c1cc(-c2ccc(Cl)cc2Cl)ccc1C1CC1]

To a mixture of 2-(5-bromo-2-cyclopropylphenyl)cyclopentane-1,3-dione (0.100 g, 0.34 mmol), 2,4-dichlorophenylboronic acid (0.090 g, 0.47 mmol), [1,1'-bis(diphenylphosphino)-ferrocene]palladium(II)chloride (22 mg, 0.027 mmol) and cesium fluoride (0.152 g, 1.0 mmol) is added 1,2-dimethoxyethane (1 ml). After evacuating and flushing with nitrogen (×3) the mixture is heated at 160° C. for 15 minutes under microwave irradiation. After dilution with distilled water the crude product is extracted with ethyl acetate (×3), and the organic phase is washed with brine, dried over magnesium sulfate and concentrated in vacuo. The crude product is then purified by flash column chromatography on silica gel (isohexane/ethyl acetate eluant) and further triturated with hexanes to afford 2-(2',4'-dichloro-4-cyclopropyl-biphenyl-3-yl)-cyclopentane-1,3-dione as a white powder.

Additional compounds in Table T1 below are prepared by similar methods using appropriate starting materials.

TABLE T1

| Compound Number | Structure | $^1$H NMR (CDCl$_3$ unless stated) or other physical data |
|---|---|---|
| T-1 | 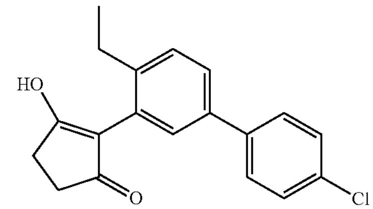 [SMILES: CCc1ccc(-c2ccc(Cl)cc2)cc1C1=C(O)CCC1=O] | δ 7.50 (m, 3H), 7.40 (m, 3H), 7.20 (d, 1H), 2.70 (br. 4H), 2.55 (q, 2H), 1.15 (t, 3H). |
| T-2 | 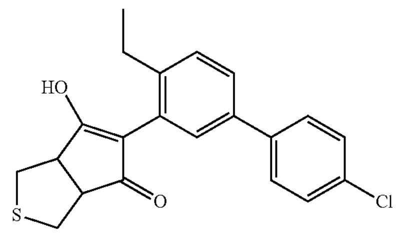 [SMILES: CCc1ccc(-c2ccc(Cl)cc2)cc1C1=C(O)C2CSCC2C1=O] | d$_4$-MeOH: δ 7.58-7.56 (m, 2H), 7.50 (dd, 1H), 7.41-7.39 (m, 2H), 7.35 (d, 1H), 7.24-7.23 (m, 1H), 3.44 (d, 2H), 3.11-3.08 (d, 2H), 3.02-2.97 (m, 2H), 2.53 (q, 2H), 1.11 (t, 3H). |
| T-3 | 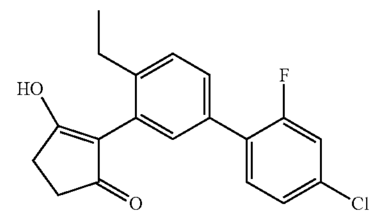 [SMILES: CCc1ccc(-c2ccc(Cl)cc2F)cc1C1=C(O)CCC1=O] | d$_4$-MeOH: δ 7.47 (tm 1H), 7.44-7.41 (m, 1H), 7.35 (d, 1H), 7.26 (d, 2H), 7.18-7.17 (m, 1H), 2.67 (s, 4H), 2.54 (q, 2H), 1.14 (t, 3H). |
| T-4 | 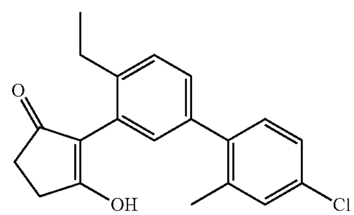 [SMILES: CCc1ccc(-c2ccc(Cl)cc2C)cc1C1=C(O)CCC1=O] | LCMS: t$_r$ = 1.57 mins, MH$^+$ = 327.1 |
| T-5 | 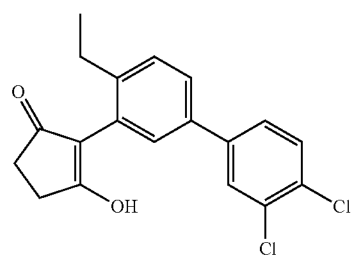 [SMILES: CCc1ccc(-c2ccc(Cl)c(Cl)c2)cc1C1=C(O)CCC1=O] | LCMS: t$_r$ = 1.60 mins, MH$^+$ = 347.1 |
| T-6 | 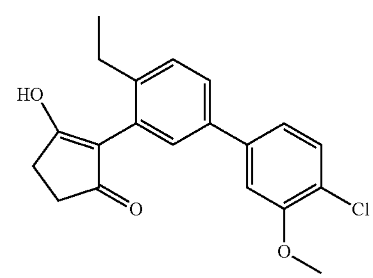 [SMILES: CCc1ccc(-c2ccc(Cl)c(OC)c2)cc1C1=C(O)CCC1=O] | LCMS: t$_r$ = 1.49 mins, MH$^+$ = 343.1 |

TABLE T1-continued

| Compound Number | Structure | $^1$H NMR (CDCl$_3$ unless stated) or other physical data |
|---|---|---|
| T-7 | 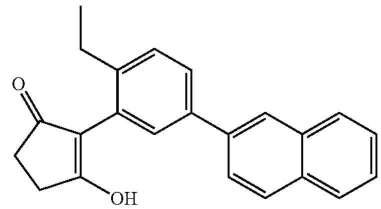 [SMILES: CCc1ccc(-c2ccc3ccccc3c2)cc1C1=C(O)CCC1=O] | LCMS: t$_r$ = 1.56 mins, MH$^+$ = 329.1 |
| T-8 | 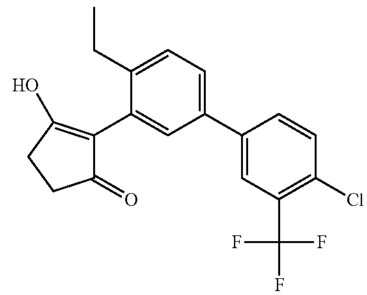 [SMILES: CCc1ccc(-c2ccc(Cl)c(C(F)(F)F)c2)cc1C1=C(O)CCC1=O] | LCMS: t$_r$ = 1.63 mins, MH$^+$ = 381.1 |
| T-9 | 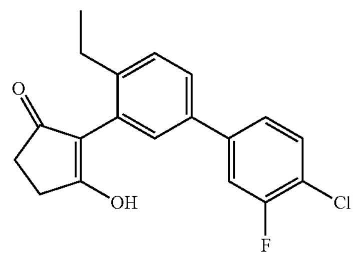 [SMILES: CCc1ccc(-c2ccc(Cl)c(F)c2)cc1C1=C(O)CCC1=O] | LCMS: t$_r$ = 1.53 mins, MH$^+$ = 331.1 |
| T-10 | 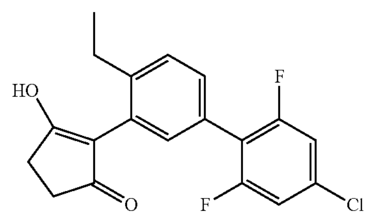 [SMILES: CCc1ccc(-c2c(F)cc(Cl)cc2F)cc1C1=C(O)CCC1=O] | LCMS: t$_r$ = 1.54 mins, MH$^+$ = 349.1 |
| T-11 | 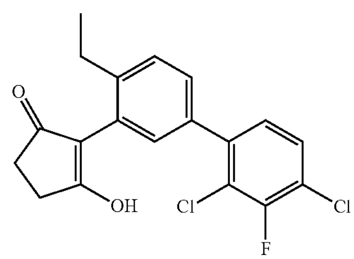 [SMILES: CCc1ccc(-c2ccc(Cl)c(F)c2Cl)cc1C1=C(O)CCC1=O] | LCMS: t$_r$ = 1.60 mins, MH$^+$ = 365.0 |
| T-12 | 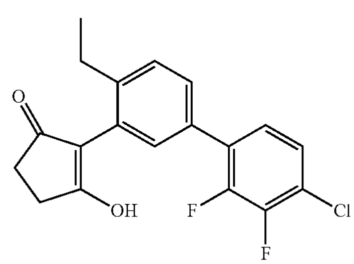 | LCMS: t$_r$ = 1.55 mins, MH$^+$ = 349.1 |

TABLE T1-continued

| Compound Number | Structure | ¹H NMR (CDCl₃ unless stated) or other physical data |
|---|---|---|
| T-13 | 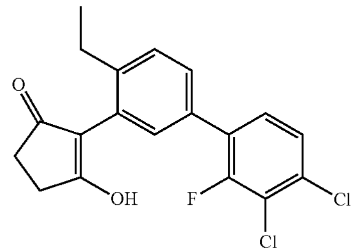 [SMILES: CCc1ccc(-c2ccc(Cl)c(Cl)c2F)cc1C1=C(O)CCC1=O] | LCMS: $t_r$ = 1.61 mins, MH⁺ = 365.0 |
| T-14 | 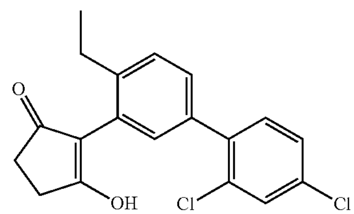 [SMILES: CCc1ccc(-c2ccc(Cl)cc2Cl)cc1C1=C(O)CCC1=O] | LCMS: $t_r$ = 1.59 mins, MH⁺ = 347.1 |
| T-15 | 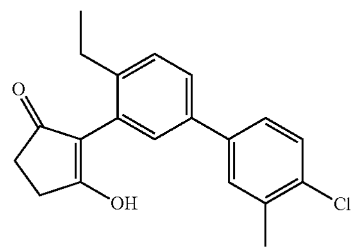 [SMILES: CCc1ccc(-c2ccc(Cl)c(C)c2)cc1C1=C(O)CCC1=O] | LCMS: $t_r$ = 1.59 mins, MH⁺ = 327.1 |
| T-16 | 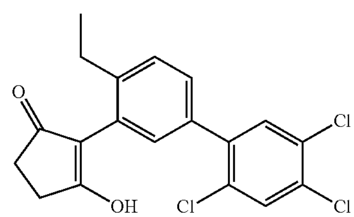 [SMILES: CCc1ccc(-c2cc(Cl)c(Cl)cc2Cl)cc1C1=C(O)CCC1=O] | LCMS: $t_r$ = 1.69 mins, MH⁺ = 381.0 |
| T-17 | 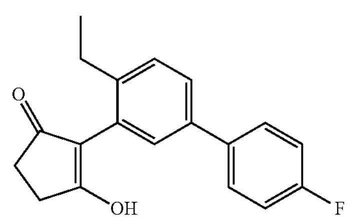 [SMILES: CCc1ccc(-c2ccc(F)cc2)cc1C1=C(O)CCC1=O] | LCMS: $t_r$ = 1.41 mins, MH⁺ = 297.1 |
| T-18 | 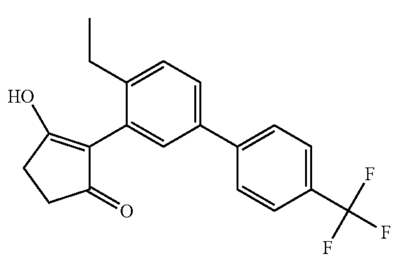 [SMILES: CCc1ccc(-c2ccc(C(F)(F)F)cc2)cc1C1=C(O)CCC1=O] | δ 7.65-7.60 (m, 4H), 7.48 (d, 1H), 7.34 (d, 1H), 7.29 (s, 1H), 2.62 (s, 4H), 2.51 (q, 2H), 1.13 (t, 3H). |

TABLE T1-continued

| Compound Number | Structure | ¹H NMR (CDCl₃ unless stated) or other physical data |
|---|---|---|
| T-19 | 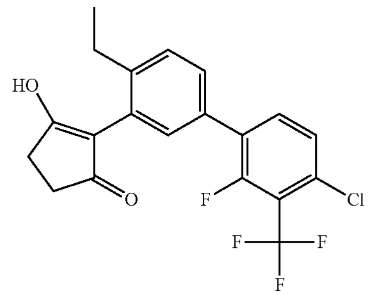 [SMILES: CCc1ccc(-c2ccc(Cl)c(C(F)(F)F)c2F)cc1C1=C(O)CCC1=O] | LCMS: $t_r$ = 1.64 mins, MH⁺ = 399.1 |
| T-20 | 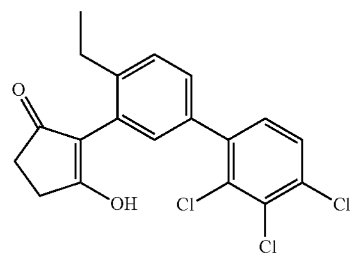 [SMILES: CCc1ccc(-c2ccc(Cl)c(Cl)c2Cl)cc1C1=C(O)CCC1=O] | LCMS: $t_r$ = 1.67 mins, MH⁺ = 381.0 |
| T-21 | 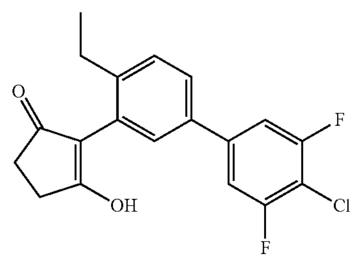 [SMILES: CCc1ccc(-c2cc(F)c(Cl)c(F)c2)cc1C1=C(O)CCC1=O] | LCMS: $t_r$ = 1.56 mins, MH⁺ = 349.1 |
| T-22 | 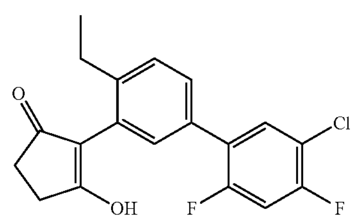 [SMILES: CCc1ccc(-c2cc(Cl)c(F)cc2F)cc1C1=C(O)CCC1=O] | LCMS: $t_r$ = 1.54 mins, MH⁺ = 349.1 |
| T-23 | 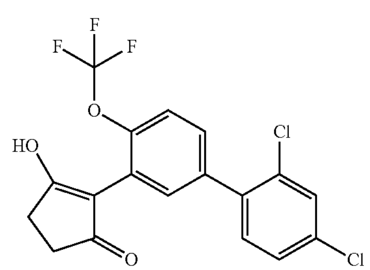 [SMILES: O=C1CCC(O)=C1c1cc(-c2ccc(Cl)cc2Cl)ccc1OC(F)(F)F] | δ 7.37-7.29 (m) 7.29-7.24 (m, 3H), 7.04-6.97 (m, 3H), 6.90 (d, 1H), 6.86 (d, 1H), 5.68 (br. s, 1H), 1.59 (s, 6H), 1.44 (s, 6H) |
| T-24 | 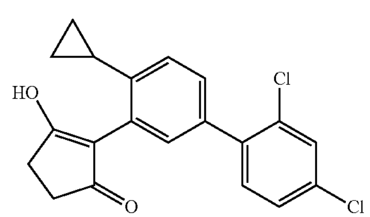 [SMILES: O=C1CCC(O)=C1c1cc(-c2ccc(Cl)cc2Cl)ccc1C1CC1] | δ 7.48 (s, 1H), 7.34 (dd, 1H), 7.26 (d, 1H), 7.18 (s, 1H), 6.99 (d, 1H), 6.72 (br. s, 1H), 2.84-2.61 (m, 4H), 1.88-1.79 (m, 1H), 0.98 (dd, 2H), 0.80-0.65 (m, 2H). |

It should be noted that certain compounds of the invention exist as a mixture of isomers, including atropisomers, noted above, under the conditions used to obtain the $^1$H NMR data. Where this has occurred, the characterising data are reported for all isomers present at ambient temperature in the specified solvent. Unless otherwise stated, proton NMR spectra were recorded at ambient temperature. Compounds characterised by HPLC-MS were analysed using the method described below.

Compounds characterised by HPLC-MS were analysed using an Waters 2777 injector with a 1525 micro pump HPLC equipped with a Waters Atlantis dC18 IS column (column length 20 mm, internal diameter of column 3 mm, particle size 3 micron), Waters 2996 photodiode array, Waters 2420 ELSD and Micromass ZQ2000. The analysis was conducted using a three minute run time, according to the following gradient table:

| Time (mins) | Solvent A (%) | Solvent B (%) | Flow (ml/mn) |
|---|---|---|---|
| 0.00 | 95.0 | 5 | 1.300 |
| 2.50 | 0.0 | 100 | 1.300 |
| 2.80 | 0.00 | 100 | 1.300 |
| 2.90 | 95.0 | 5 | 1.300 |

Solvent A: H$_2$O with 0.05% TFA
Solvent B: CH$_3$CN with 0.05% TFA

The characteristic values obtained for each compound were the retention time (rt, recorded in minutes) and the molecular ion (typically the cation MH$^+$), as listed in Table T1.

The compounds of the following Tables 1 to 20 can be obtained in an analogous manner.

Table 1 covers 378 compounds of the type A-1

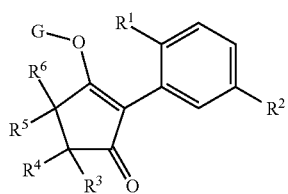

A-1 wherein G is hydrogen, R$^3$, R$^4$, R$^5$ and R$^6$ are hydrogen, and R$^1$ and R$^2$ are as defined in Table 1.

| Compound Number | R$^1$ | R$^2$ |
|---|---|---|
| 1.001 | ethyl | phenyl |
| 1.002 | ethyl | 2-fluorophenyl |
| 1.003 | ethyl | 3-fluorophenyl |
| 1.004 | ethyl | 4-fluorophenyl |
| 1.005 | ethyl | 2-chlorophenyl |
| 1.006 | ethyl | 3-chlorophenyl |
| 1.007 | ethyl | 4-chlorophenyl |
| 1.008 | ethyl | 2-bromophenyl |
| 1.009 | ethyl | 3-bromophenyl |
| 1.010 | ethyl | 4-bromophenyl |
| 1.011 | ethyl | 2-methylphenyl |
| 1.012 | ethyl | 3-methylphenyl |
| 1.013 | ethyl | 4-methylphenyl |
| 1.014 | ethyl | 4-ethylphenyl |
| 1.015 | ethyl | 4-isopropylphenyl |
| 1.016 | ethyl | 4-isobutylphenyl |
| 1.017 | ethyl | 4-tert-butylphenyl |
| 1.018 | ethyl | 2-cyanophenyl |
| 1.019 | ethyl | 3-cyanophenyl |
| 1.020 | ethyl | 4-cyanophenyl |
| 1.021 | ethyl | 2-methoxyphenyl |
| 1.022 | ethyl | 3-methoxyphenyl |
| 1.023 | ethyl | 4-methoxyphenyl |
| 1.024 | ethyl | 2-trifluoromethylphenyl |
| 1.025 | ethyl | 3-trifluoromethylphenyl |
| 1.026 | ethyl | 4-trifluoromethylphenyl |
| 1.027 | ethyl | 4-trifluoromethoxyphenyl |
| 1.028 | ethyl | 4-difluoromethoxyphenyl |
| 1.029 | ethyl | 4-methylthiophenyl |
| 1.030 | ethyl | 4-methylsulfinylphenyl |
| 1.031 | ethyl | 4-methylsulfonylphenyl |
| 1.032 | ethyl | 4-trifluoromethylthiophenyl |
| 1.033 | ethyl | 4-trifluoromethylsulfinylphenyl |
| 1.034 | ethyl | 4-trifluoromethylsulfonylphenyl |
| 1.035 | ethyl | 2,3-difluorophenyl |
| 1.036 | ethyl | 2,4-difluorophenyl |
| 1.037 | ethyl | 2,5-difluorophenyl |
| 1.038 | ethyl | 2,6-difluorophenyl |
| 1.039 | ethyl | 3,4-difluorophenyl |
| 1.040 | ethyl | 3,5-difluorophenyl |
| 1.041 | ethyl | 2,3-dichlorophenyl |
| 1.042 | ethyl | 2,4-dichlorophenyl |
| 1.043 | ethyl | 2,5-dichlorophenyl |
| 1.044 | ethyl | 2,6-dichlorophenyl |
| 1.045 | ethyl | 3,4-dichlorophenyl |
| 1.046 | ethyl | 3,5-dichlorophenyl |
| 1.047 | ethyl | 2,3,4-trichlorophenyl |
| 1.048 | ethyl | 2,3,5-trichlorophenyl |
| 1.049 | ethyl | 2,3,6-trichlorophenyl |
| 1.050 | ethyl | 2,4,5-trichlorophenyl |
| 1.051 | ethyl | 2,4,6-trichlorophenyl |
| 1.052 | ethyl | 3,4,5-trichlorophenyl |
| 1.053 | ethyl | 2-chloro-3-fluorophenyl |
| 1.054 | ethyl | 2-chloro-4-fluorophenyl |
| 1.055 | ethyl | 2-chloro-4-fluorophenyl |
| 1.056 | ethyl | 2-chloro-4-fluorophenyl |
| 1.057 | ethyl | 3-chloro-2-fluorophenyl |
| 1.058 | ethyl | 3-chloro-4-fluorophenyl |
| 1.059 | ethyl | 3-chloro-5-fluorophenyl |
| 1.060 | ethyl | 4-chloro-2-fluorophenyl |
| 1.061 | ethyl | 4-chloro-3-fluorophenyl |
| 1.062 | ethyl | 5-chloro-2-fluorophenyl |
| 1.063 | ethyl | 4-chloro-2-methylphenyl |
| 1.064 | ethyl | 4-chloro-3-methylphenyl |
| 1.065 | ethyl | 4-chloro-2-trifluoromethylphenyl |
| 1.066 | ethyl | 4-chloro-3-trifluoromethylphenyl |
| 1.067 | ethyl | 4-chloro-2-cyanophenyl |
| 1.068 | ethyl | 4-chloro-3-cyanophenyl |
| 1.069 | ethyl | 4-chloro-2-methoxyphenyl |
| 1.070 | ethyl | 4-chloro-3-methoxyphenyl |
| 1.071 | ethyl | 4-fluoro-2-methylphenyl |
| 1.072 | ethyl | 4-fluoro-3-methylphenyl |
| 1.073 | ethyl | 4-fluoro-2-trifluoromethylphenyl |
| 1.074 | ethyl | 4-fluoro-3-trifluoromethylphenyl |
| 1.075 | ethyl | 2-fluoro-4-trifluoromethylphenyl |
| 1.076 | ethyl | 3-fluoro-4-trifluoromethylphenyl |
| 1.077 | ethyl | 2,3,4-trifluorophenyl |
| 1.078 | ethyl | 2,3,5-trifluorophenyl |
| 1.079 | ethyl | 2,3,6-trifluorophenyl |
| 1.080 | ethyl | 2,4,5-trifluorophenyl |
| 1.081 | ethyl | 2,4,6-trifluorophenyl |
| 1.082 | ethyl | 3,4,5-trifluorophenyl |
| 1.083 | ethyl | 3,4-dichloro-2-fluorophenyl |
| 1.084 | ethyl | 3,4-dichoro-5-fluorophenyl |
| 1.085 | ethyl | 4,5-dichloro-2-fluorophenyl |
| 1.086 | ethyl | 2-chloro-3,4-difluorophenyl |
| 1.087 | ethyl | 2-chloro-4,5-difluorophenyl |
| 1.088 | ethyl | 2-chloro-4,6-difluorophenyl |
| 1.089 | ethyl | 3-chloro-4,5-difluorophenyl |
| 1.090 | ethyl | 3,4-methylenedioxyphenyl |
| 1.091 | ethyl | benzo[1,3]diox-5-yl |
| 1.092 | ethyl | 2,3-dihydrobenzo[1,4]dioxin-6-yl |

-continued

| Compound Number | R¹ | R² |
|---|---|---|
| 1.093 | ethyl | 2-naphthyl |
| 1.094 | ethyl | 2-pyridyl |
| 1.095 | ethyl | 3-pyridyl |
| 1.096 | ethyl | 4-pyridyl |
| 1.097 | ethyl | 3-chloropyridin-2-yl |
| 1.098 | ethyl | 4-chloropyridin-2-yl |
| 1.099 | ethyl | 5-chloropyridin-2-yl |
| 1.100 | ethyl | 6-chloropyridin-2-yl |
| 1.101 | ethyl | 2-chloropyridin-3-yl |
| 1.102 | ethyl | 4-chloropyridin-3-yl |
| 1.103 | ethyl | 2-chloropyridin-4-yl |
| 1.104 | ethyl | 3-chloropyridin-4-yl |
| 1.105 | ethyl | 2-chloropyridin-5-yl |
| 1.106 | ethyl | 3-chloropyridin-5-yl |
| 1.107 | ethyl | 3-methylpyridin-2-yl |
| 1.108 | ethyl | 4-methylpyridin-2-yl |
| 1.109 | ethyl | 5-methylpyridin-2-yl |
| 1.110 | ethyl | 6-methylpyridin-2-yl |
| 1.111 | ethyl | 2-methylpyridin-3-yl |
| 1.112 | ethyl | 4-methylpyridin-3-yl |
| 1.113 | ethyl | 2-methylpyridin-4-yl |
| 1.114 | ethyl | 3-methylpyridin-4-yl |
| 1.115 | ethyl | 2-methylpyridin-5-yl |
| 1.116 | ethyl | 3-methylpyridinyl-5-yl |
| 1.117 | ethyl | 2-trifluoromethylpyridin-5-yl |
| 1.118 | ethyl | 3-trifluoromethylpyridin-5-yl |
| 1.119 | ethyl | 2,6-dichloropyridin-3-yl |
| 1.120 | ethyl | 2-chloro-4-methylpyridin-5-yl |
| 1.121 | ethyl | 6-chloro-2-methylpyridin-3-yl |
| 1.122 | ethyl | 5-chlorothiophen-2-yl |
| 1.123 | ethyl | 2-chlorothiophen-3-yl |
| 1.124 | ethyl | 2,5-dichlorothiophen-3-yl |
| 1.125 | ethyl | 1-methylpyrazol-4-yl |
| 1.126 | ethyl | 4-chloropyrazol-1-yl |
| 1.127 | difluoromethoxy | phenyl |
| 1.128 | difluoromethoxy | 2-fluorophenyl |
| 1.129 | difluoromethoxy | 3-fluorophenyl |
| 1.130 | difluoromethoxy | 4-fluorophenyl |
| 1.131 | difluoromethoxy | 2-chlorophenyl |
| 1.132 | difluoromethoxy | 3-chlorophenyl |
| 1.133 | difluoromethoxy | 4-chlorophenyl |
| 1.134 | difluoromethoxy | 2-bromophenyl |
| 1.135 | difluoromethoxy | 3-bromophenyl |
| 1.136 | difluoromethoxy | 4-bromophenyl |
| 1.137 | difluoromethoxy | 2-methylphenyl |
| 1.138 | difluoromethoxy | 3-methylphenyl |
| 1.139 | difluoromethoxy | 4-methylphenyl |
| 1.140 | difluoromethoxy | 4-ethylphenyl |
| 1.141 | difluoromethoxy | 4-isopropylphenyl |
| 1.142 | difluoromethoxy | 4-isobutylphenyl |
| 1.143 | difluoromethoxy | 4-tert-butylphenyl |
| 1.144 | difluoromethoxy | 2-cyanophenyl |
| 1.145 | difluoromethoxy | 3-cyanophenyl |
| 1.146 | difluoromethoxy | 4-cyanophenyl |
| 1.147 | difluoromethoxy | 2-methoxyphenyl |
| 1.148 | difluoromethoxy | 3-methoxyphenyl |
| 1.149 | difluoromethoxy | 4-methoxyphenyl |
| 1.150 | difluoromethoxy | 2-trifluoromethylphenyl |
| 1.151 | difluoromethoxy | 3-trifluoromethylphenyl |
| 1.152 | difluoromethoxy | 4-trifluoromethylphenyl |
| 1.153 | difluoromethoxy | 4-trifluoromethoxyphenyl |
| 1.154 | difluoromethoxy | 4-difluoromethoxyphenyl |
| 1.155 | difluoromethoxy | 4-methylthiophenyl |
| 1.156 | difluoromethoxy | 4-methylsulfinylphenyl |
| 1.157 | difluoromethoxy | 4-methylsulfonylphenyl |
| 1.158 | difluoromethoxy | 4-trifluoromethylthiophenyl |
| 1.159 | difluoromethoxy | 4-trifluoromethylsulfinylphenyl |
| 1.160 | difluoromethoxy | 4-trifluoromethylsulfonylphenyl |
| 1.161 | difluoromethoxy | 2,3-difluorophenyl |
| 1.162 | difluoromethoxy | 2,4-difluorophenyl |
| 1.163 | difluoromethoxy | 2,5-difluorophenyl |
| 1.164 | difluoromethoxy | 2,6-difluorophenyl |
| 1.165 | difluoromethoxy | 3,4-difluorophenyl |
| 1.166 | difluoromethoxy | 3,5-difluorophenyl |
| 1.167 | difluoromethoxy | 2,3-dichlorophenyl |
| 1.168 | difluoromethoxy | 2,4-dichlorophenyl |
| 1.169 | difluoromethoxy | 2,5-dichlorophenyl |
| 1.170 | difluoromethoxy | 2,6-dichlorophenyl |
| 1.171 | difluoromethoxy | 3,4-dichlorophenyl |
| 1.172 | difluoromethoxy | 3,5-dichlorophenyl |
| 1.173 | difluoromethoxy | 2,3,4-trichlorophenyl |
| 1.174 | difluoromethoxy | 2,3,5-trichlorophenyl |
| 1.175 | difluoromethoxy | 2,3,6-trichlorophenyl |
| 1.176 | difluoromethoxy | 2,4,5-trichlorophenyl |
| 1.177 | difluoromethoxy | 2,4,6-trichlorophenyl |
| 1.178 | difluoromethoxy | 3,4,5-trichlorophenyl |
| 1.179 | difluoromethoxy | 2-chloro-3-fluorophenyl |
| 1.180 | difluoromethoxy | 2-chloro-4-fluorophenyl |
| 1.181 | difluoromethoxy | 2-chloro-4-fluorophenyl |
| 1.182 | difluoromethoxy | 2-chloro-4-fluorophenyl |
| 1.183 | difluoromethoxy | 3-chloro-2-fluorophenyl |
| 1.184 | difluoromethoxy | 3-chloro-4-fluorophenyl |
| 1.185 | difluoromethoxy | 3-chloro-5-fluorophenyl |
| 1.186 | difluoromethoxy | 4-chloro-2-fluorophenyl |
| 1.187 | difluoromethoxy | 4-chloro-3-fluorophenyl |
| 1.188 | difluoromethoxy | 5-chloro-2-fluorophenyl |
| 1.189 | difluoromethoxy | 4-chloro-2-methylphenyl |
| 1.190 | difluoromethoxy | 4-chloro-3-methylphenyl |
| 1.191 | difluoromethoxy | 4-chloro-2-trifluoromethylphenyl |
| 1.192 | difluoromethoxy | 4-chloro-3-trifluoromethylphenyl |
| 1.193 | difluoromethoxy | 4-chloro-2-cyanophenyl |
| 1.194 | difluoromethoxy | 4-chloro-3-cyanophenyl |
| 1.195 | difluoromethoxy | 4-chloro-2-methoxyphenyl |
| 1.196 | difluoromethoxy | 4-chloro-3-methoxyphenyl |
| 1.197 | difluoromethoxy | 4-fluoro-2-methylphenyl |
| 1.198 | difluoromethoxy | 4-fluoro-3-methylphenyl |
| 1.199 | difluoromethoxy | 4-fluoro-2-trifluoromethylphenyl |
| 1.200 | difluoromethoxy | 4-fluoro-3-trifluoromethylphenyl |
| 1.201 | difluoromethoxy | 2-fluoro-4-trifluoromethylphenyl |
| 1.202 | difluoromethoxy | 3-fluoro-4-trifluoromethylphenyl |
| 1.203 | difluoromethoxy | 2,3,4-trifluorophenyl |
| 1.204 | difluoromethoxy | 2,3,5-trifluorophenyl |
| 1.205 | difluoromethoxy | 2,3,6-trifluorophenyl |
| 1.206 | difluoromethoxy | 2,4,5-trifluorophenyl |
| 1.207 | difluoromethoxy | 2,4,6-trifluorophenyl |
| 1.208 | difluoromethoxy | 3,4,5-trifluorophenyl |
| 1.209 | difluoromethoxy | 3,4-dichloro-2-fluorophenyl |
| 1.210 | difluoromethoxy | 3,4-dichoro-5-fluorophenyl |
| 1.211 | difluoromethoxy | 4,5-dichloro-2-fluorophenyl |
| 1.212 | difluoromethoxy | 2-chloro-3,4-difluorophenyl |
| 1.213 | difluoromethoxy | 2-chloro-4,5-difluorophenyl |
| 1.214 | difluoromethoxy | 2-chloro-4,6-difluorophenyl |
| 1.215 | difluoromethoxy | 3-chloro-4,5-difluorophenyl |
| 1.216 | difluoromethoxy | 3,4-methylenedioxyphenyl |
| 1.217 | difluoromethoxy | benzo[1,3]diox-5-yl |
| 1.218 | difluoromethoxy | 2,3-dihydrobenzo[1,4]dioxin-6-yl |
| 1.219 | difluoromethoxy | 2-naphthyl |
| 1.220 | difluoromethoxy | 2-pyridyl |
| 1.221 | difluoromethoxy | 3-pyridyl |
| 1.222 | difluoromethoxy | 4-pyridyl |
| 1.223 | difluoromethoxy | 3-chloropyridin-2-yl |
| 1.224 | difluoromethoxy | 4-chloropyridin-2-yl |
| 1.225 | difluoromethoxy | 5-chloropyridin-2-yl |
| 1.226 | difluoromethoxy | 6-chloropyridin-2-yl |
| 1.227 | difluoromethoxy | 2-chloropyridin-3-yl |
| 1.228 | difluoromethoxy | 4-chloropyridin-3-yl |
| 1.229 | difluoromethoxy | 2-chloropyridin-4-yl |
| 1.230 | difluoromethoxy | 3-chloropyridin-4-yl |
| 1.231 | difluoromethoxy | 2-chloropyridin-5-yl |
| 1.232 | difluoromethoxy | 3-chloropyridin-5-yl |
| 1.233 | difluoromethoxy | 3-methylpyridin-2-yl |
| 1.234 | difluoromethoxy | 4-methylpyridin-2-yl |
| 1.235 | difluoromethoxy | 5-methylpyridin-2-yl |
| 1.236 | difluoromethoxy | 6-methylpyridin-2-yl |
| 1.237 | difluoromethoxy | 2-methylpyridin-3-yl |
| 1.238 | difluoromethoxy | 4-methylpyridin-3-yl |
| 1.239 | difluoromethoxy | 2-methylpyridin-4-yl |
| 1.240 | difluoromethoxy | 3-methylpyridin-4-yl |
| 1.241 | difluoromethoxy | 2-methylpyridin-5-yl |
| 1.242 | difluoromethoxy | 3-methylpyridinyl-5-yl |
| 1.243 | difluoromethoxy | 2-trifluoromethylpyridin-5-yl |
| 1.244 | difluoromethoxy | 3-trifluoromethylpyridin-5-yl |
| 1.245 | difluoromethoxy | 2,6-dichloropyridin-3-yl |
| 1.246 | difluoromethoxy | 2-chloro-4-methylpyridin-5-yl |

-continued

| Compound Number | R¹ | R² |
|---|---|---|
| 1.247 | difluoromethoxy | 6-chloro-2-methylpyridin-3-yl |
| 1.248 | difluoromethoxy | 5-chlorothiophen-2-yl |
| 1.249 | difluoromethoxy | 2-chlorothiophen-3-yl |
| 1.250 | difluoromethoxy | 2,5-dichlorothiophen-3-yl |
| 1.251 | difluoromethoxy | 1-methylpyrazol-4-yl |
| 1.252 | difluoromethoxy | 4-chloropyrazol-1-yl |
| 1.253 | trifluoromethoxy | phenyl |
| 1.254 | trifluoromethoxy | 2-fluorophenyl |
| 1.255 | trifluoromethoxy | 3-fluorophenyl |
| 1.256 | trifluoromethoxy | 4-fluorophenyl |
| 1.257 | trifluoromethoxy | 2-chlorophenyl |
| 1.258 | trifluoromethoxy | 3-chlorophenyl |
| 1.259 | trifluoromethoxy | 4-chlorophenyl |
| 1.260 | trifluoromethoxy | 2-bromophenyl |
| 1.261 | trifluoromethoxy | 3-bromophenyl |
| 1.262 | trifluoromethoxy | 4-bromophenyl |
| 1.263 | trifluoromethoxy | 2-methylphenyl |
| 1.264 | trifluoromethoxy | 3-methylphenyl |
| 1.265 | trifluoromethoxy | 4-methylphenyl |
| 1.266 | trifluoromethoxy | 4-ethylphenyl |
| 1.267 | trifluoromethoxy | 4-isopropylphenyl |
| 1.268 | trifluoromethoxy | 4-isobutylphenyl |
| 1.269 | trifluoromethoxy | 4-tert-butylphenyl |
| 1.270 | trifluoromethoxy | 2-cyanophenyl |
| 1.271 | trifluoromethoxy | 3-cyanophenyl |
| 1.272 | trifluoromethoxy | 4-cyanophenyl |
| 1.273 | trifluoromethoxy | 2-methoxyphenyl |
| 1.274 | trifluoromethoxy | 3-methoxyphenyl |
| 1.275 | trifluoromethoxy | 4-methoxyphenyl |
| 1.276 | trifluoromethoxy | 2-trifluoromethylphenyl |
| 1.277 | trifluoromethoxy | 3-trifluoromethylphenyl |
| 1.278 | trifluoromethoxy | 4-trifluoromethylphenyl |
| 1.279 | trifluoromethoxy | 4-trifluoromethoxyphenyl |
| 1.280 | trifluoromethoxy | 4-difluoromethoxyphenyl |
| 1.281 | trifluoromethoxy | 4-methylthiophenyl |
| 1.282 | trifluoromethoxy | 4-methylsulfinylphenyl |
| 1.283 | trifluoromethoxy | 4-methylsulfonylphenyl |
| 1.284 | trifluoromethoxy | 4-trifluoromethylthiophenyl |
| 1.285 | trifluoromethoxy | 4-trifluoromethylsulfinylphenyl |
| 1.286 | trifluoromethoxy | 4-trifluoromethylsulfonylphenyl |
| 1.287 | trifluoromethoxy | 2,3-difluorophenyl |
| 1.288 | trifluoromethoxy | 2,4-difluorophenyl |
| 1.289 | trifluoromethoxy | 2,5-difluorophenyl |
| 1.290 | trifluoromethoxy | 2,6-difluorophenyl |
| 1.291 | trifluoromethoxy | 3,4-difluorophenyl |
| 1.292 | trifluoromethoxy | 3,5-difluorophenyl |
| 1.293 | trifluoromethoxy | 2,3-dichlorophenyl |
| 1.294 | trifluoromethoxy | 2,4-dichlorophenyl |
| 1.295 | trifluoromethoxy | 2,5-dichlorophenyl |
| 1.296 | trifluoromethoxy | 2,6-dichlorophenyl |
| 1.297 | trifluoromethoxy | 3,4-dichlorophenyl |
| 1.298 | trifluoromethoxy | 3,5-dichlorophenyl |
| 1.299 | trifluoromethoxy | 2,3,4-trichlorophenyl |
| 1.300 | trifluoromethoxy | 2,3,5-trichlorophenyl |
| 1.301 | trifluoromethoxy | 2,3,6-trichlorophenyl |
| 1.302 | trifluoromethoxy | 2,4,5-trichlorophenyl |
| 1.303 | trifluoromethoxy | 2,4,6-trichlorophenyl |
| 1.304 | trifluoromethoxy | 3,4,5-trichlorophenyl |
| 1.305 | trifluoromethoxy | 2-chloro-3-fluorophenyl |
| 1.306 | trifluoromethoxy | 2-chloro-4-fluorophenyl |
| 1.307 | trifluoromethoxy | 2-chloro-4-fluorophenyl |
| 1.308 | trifluoromethoxy | 2-chloro-4-fluorophenyl |
| 1.309 | trifluoromethoxy | 3-chloro-2-fluorophenyl |
| 1.310 | trifluoromethoxy | 3-chloro-4-fluorophenyl |
| 1.311 | trifluoromethoxy | 3-chloro-5-fluorophenyl |
| 1.312 | trifluoromethoxy | 4-chloro-2-fluorophenyl |
| 1.313 | trifluoromethoxy | 4-chloro-3-fluorophenyl |
| 1.314 | trifluoromethoxy | 5-chloro-2-fluorophenyl |
| 1.315 | trifluoromethoxy | 4-chloro-2-methylphenyl |
| 1.316 | trifluoromethoxy | 4-chloro-3-methylphenyl |
| 1.317 | trifluoromethoxy | 4-chloro-2-trifluoromethylphenyl |
| 1.318 | trifluoromethoxy | 4-chloro-3-trifluoromethylphenyl |
| 1.319 | trifluoromethoxy | 4-chloro-2-cyanophenyl |
| 1.320 | trifluoromethoxy | 4-chloro-3-cyanophenyl |
| 1.321 | trifluoromethoxy | 4-chloro-2-methoxyphenyl |
| 1.322 | trifluoromethoxy | 4-chloro-3-methoxyphenyl |
| 1.323 | trifluoromethoxy | 4-fluoro-2-methylphenyl |
| 1.324 | trifluoromethoxy | 4-fluoro-3-methylphenyl |
| 1.325 | trifluoromethoxy | 4-fluoro-2-trifluoromethylphenyl |
| 1.326 | trifluoromethoxy | 4-fluoro-3-trifluoromethylphenyl |
| 1.327 | trifluoromethoxy | 2-fluoro-4-trifluoromethylphenyl |
| 1.328 | trifluoromethoxy | 3-fluoro-4-trifluoromethylphenyl |
| 1.329 | trifluoromethoxy | 2,3,4-trifluorophenyl |
| 1.330 | trifluoromethoxy | 2,3,5-trifluorophenyl |
| 1.331 | trifluoromethoxy | 2,3,6-trifluorophenyl |
| 1.332 | trifluoromethoxy | 2,4,5-trifluorophenyl |
| 1.333 | trifluoromethoxy | 2,4,6-trifluorophenyl |
| 1.337 | trifluoromethoxy | 3,4,5-trifluorophenyl |
| 1.335 | trifluoromethoxy | 3,4-dichloro-2-fluorophenyl |
| 1.336 | trifluoromethoxy | 3,4-dichoro-5-fluorophenyl |
| 1.337 | trifluoromethoxy | 4,5-dichloro-2-fluorophenyl |
| 1.338 | trifluoromethoxy | 2-chloro-3,4-difluorophenyl |
| 1.339 | trifluoromethoxy | 2-chloro-4,5-difluorophenyl |
| 1.340 | trifluoromethoxy | 2-chloro-4,6-difluorophenyl |
| 1.341 | trifluoromethoxy | 3-chloro-4,5-difluorophenyl |
| 1.342 | trifluoromethoxy | 3,4-methylenedioxyphenyl |
| 1.343 | trifluoromethoxy | benzo[1,3]diox-5-yl |
| 1.344 | trifluoromethoxy | 2,3-dihydrobenzo[1,4]dioxin-6-yl |
| 1.345 | trifluoromethoxy | 2-naphthyl |
| 1.346 | trifluoromethoxy | 2-pyridyl |
| 1.347 | trifluoromethoxy | 3-pyridyl |
| 1.348 | trifluoromethoxy | 4-pyridyl |
| 1.349 | trifluoromethoxy | 3-chloropyridin-2-yl |
| 1.350 | trifluoromethoxy | 4-chloropyridin-2-yl |
| 1.351 | trifluoromethoxy | 5-chloropyridin-2-yl |
| 1.352 | trifluoromethoxy | 6-chloropyridin-2-yl |
| 1.353 | trifluoromethoxy | 2-chloropyridin-3-yl |
| 1.354 | trifluoromethoxy | 4-chloropyridin-3-yl |
| 1.355 | trifluoromethoxy | 2-chloropyridin-4-yl |
| 1.356 | trifluoromethoxy | 3-chloropyridin-4-yl |
| 1.357 | trifluoromethoxy | 2-chloropyridin-5-yl |
| 1.358 | trifluoromethoxy | 3-chloropyridin-5-yl |
| 1.359 | trifluoromethoxy | 3-methylpyridin-2-yl |
| 1.360 | trifluoromethoxy | 4-methylpyridin-2-yl |
| 1.361 | trifluoromethoxy | 5-methylpyridin-2-yl |
| 1.362 | trifluoromethoxy | 6-methylpyridin-2-yl |
| 1.363 | trifluoromethoxy | 2-methylpyridin-3-yl |
| 1.364 | trifluoromethoxy | 4-methylpyridin-3-yl |
| 1.365 | trifluoromethoxy | 2-methylpyridin-4-yl |
| 1.366 | trifluoromethoxy | 3-methylpyridin-4-yl |
| 1.367 | trifluoromethoxy | 2-methylpyridin-5-yl |
| 1.368 | trifluoromethoxy | 3-methylpyridinyl-5-yl |
| 1.369 | trifluoromethoxy | 2-trifluoromethylpyridin-5-yl |
| 1.370 | trifluoromethoxy | 3-trifluoromethylpyridin-5-yl |
| 1.371 | trifluoromethoxy | 2,6-dichloropyridin-3-yl |
| 1.372 | trifluoromethoxy | 2-chloro-4-methylpyridin-5-yl |
| 1.373 | trifluoromethoxy | 6-chloro-2-methylpyridin-3-yl |
| 1.374 | trifluoromethoxy | 5-chlorothiophen-2-yl |
| 1.375 | trifluoromethoxy | 2-chlorothiophen-3-yl |
| 1.376 | trifluoromethoxy | 2,5-dichlorothiophen-3-yl |
| 1.377 | trifluoromethoxy | 1-methylpyrazol-4-yl |
| 1.378 | trifluoromethoxy | 4-chloropyrazol-1-yl |
| 1.379 | cyclopropyl | phenyl |
| 1.380 | cyclopropyl | 2-fluorophenyl |
| 1.381 | cyclopropyl | 3-fluorophenyl |
| 1.382 | cyclopropyl | 4-fluorophenyl |
| 1.383 | cyclopropyl | 2-chlorophenyl |
| 1.384 | cyclopropyl | 3-chlorophenyl |
| 1.385 | cyclopropyl | 4-chlorophenyl |
| 1.386 | cyclopropyl | 2-bromophenyl |
| 1.387 | cyclopropyl | 3-bromophenyl |
| 1.388 | cyclopropyl | 4-bromophenyl |
| 1.389 | cyclopropyl | 2-methylphenyl |
| 1.390 | cyclopropyl | 3-methylphenyl |
| 1.391 | cyclopropyl | 4-methylphenyl |
| 1.392 | cyclopropyl | 4-ethylphenyl |
| 1.393 | cyclopropyl | 4-isopropylphenyl |
| 1.394 | cyclopropyl | 4-isobutylphenyl |
| 1.395 | cyclopropyl | 4-tert-butylphenyl |
| 1.396 | cyclopropyl | 2-cyanophenyl |
| 1.397 | cyclopropyl | 3-cyanophenyl |
| 1.398 | cyclopropyl | 4-cyanophenyl |
| 1.399 | cyclopropyl | 2-methoxyphenyl |
| 1.400 | cyclopropyl | 3-methoxyphenyl |

-continued

| Compound Number | R¹ | R² |
|---|---|---|
| 1.401 | cyclopropyl | 4-methoxyphenyl |
| 1.402 | cyclopropyl | 2-trifluoromethylphenyl |
| 1.403 | cyclopropyl | 3-trifluoromethylphenyl |
| 1.404 | cyclopropyl | 4-trifluoromethylphenyl |
| 1.405 | cyclopropyl | 4-trifluoromethoxyphenyl |
| 1.406 | cyclopropyl | 4-difluoromethoxyphenyl |
| 1.407 | cyclopropyl | 4-methylthiophenyl |
| 1.408 | cyclopropyl | 4-methylsulfinylphenyl |
| 1.409 | cyclopropyl | 4-methylsulfonylphenyl |
| 1.410 | cyclopropyl | 4-trifluoromethylthiophenyl |
| 1.411 | cyclopropyl | 4-trifluoromethylsulfinylphenyl |
| 1.412 | cyclopropyl | 4-trifluoromethylsulfonylphenyl |
| 1.413 | cyclopropyl | 2,3-difluorophenyl |
| 1.414 | cyclopropyl | 2,4-difluorophenyl |
| 1.415 | cyclopropyl | 2,5-difluorophenyl |
| 1.416 | cyclopropyl | 2,6-difluorophenyl |
| 1.417 | cyclopropyl | 3,4-difluorophenyl |
| 1.418 | cyclopropyl | 3,5-difluorophenyl |
| 1.419 | cyclopropyl | 2,3-dichlorophenyl |
| 1.420 | cyclopropyl | 2,4-dichlorophenyl |
| 1.421 | cyclopropyl | 2,5-dichlorophenyl |
| 1.422 | cyclopropyl | 2,6-dichlorophenyl |
| 1.423 | cyclopropyl | 3,4-dichlorophenyl |
| 1.424 | cyclopropyl | 3,5-dichlorophenyl |
| 1.425 | cyclopropyl | 2,3,4-trichlorophenyl |
| 1.426 | cyclopropyl | 2,3,5-trichlorophenyl |
| 1.427 | cyclopropyl | 2,3,6-trichlorophenyl |
| 1.428 | cyclopropyl | 2,4,5-trichlorophenyl |
| 1.429 | cyclopropyl | 2,4,6-trichlorophenyl |
| 1.430 | cyclopropyl | 3,4,5-trichlorophenyl |
| 1.431 | cyclopropyl | 2-chloro-3-fluorophenyl |
| 1.432 | cyclopropyl | 2-chloro-4-fluorophenyl |
| 1.433 | cyclopropyl | 2-chloro-4-fluorophenyl |
| 1.434 | cyclopropyl | 2-chloro-4-fluorophenyl |
| 1.435 | cyclopropyl | 3-chloro-2-fluorophenyl |
| 1.436 | cyclopropyl | 3-chloro-4-fluorophenyl |
| 1.437 | cyclopropyl | 3-chloro-5-fluorophenyl |
| 1.438 | cyclopropyl | 4-chloro-2-fluorophenyl |
| 1.439 | cyclopropyl | 4-chloro-3-fluorophenyl |
| 1.440 | cyclopropyl | 5-chloro-2-fluorophenyl |
| 1.441 | cyclopropyl | 4-chloro-2-methylphenyl |
| 1.442 | cyclopropyl | 4-chloro-3-methylphenyl |
| 1.443 | cyclopropyl | 4-chloro-2-trifluoromethylphenyl |
| 1.444 | cyclopropyl | 4-chloro-3-trifluoromethylphenyl |
| 1.445 | cyclopropyl | 4-chloro-2-cyanophenyl |
| 1.446 | cyclopropyl | 4-chloro-3-cyanophenyl |
| 1.447 | cyclopropyl | 4-chloro-2-methoxyphenyl |
| 1.448 | cyclopropyl | 4-chloro-3-methoxyphenyl |
| 1.449 | cyclopropyl | 4-fluoro-2-methylphenyl |
| 1.450 | cyclopropyl | 4-fluoro-3-methylphenyl |
| 1.451 | cyclopropyl | 4-fluoro-2-trifluoromethylphenyl |
| 1.452 | cyclopropyl | 4-fluoro-3-trifluoromethylphenyl |
| 1.453 | cyclopropyl | 2-fluoro-4-trifluoromethylphenyl |
| 1.454 | cyclopropyl | 3-fluoro-4-trifluoromethylphenyl |
| 1.455 | cyclopropyl | 2,3,4-trifluorophenyl |
| 1.456 | cyclopropyl | 2,3,5-trifluorophenyl |
| 1.457 | cyclopropyl | 2,3,6-trifluorophenyl |
| 1.458 | cyclopropyl | 2,4,5-trifluorophenyl |
| 1.459 | cyclopropyl | 2,4,6-trifluorophenyl |
| 1.450 | cyclopropyl | 3,4,5-trifluorophenyl |
| 1.451 | cyclopropyl | 3,4-dichloro-2-fluorophenyl |
| 1.452 | cyclopropyl | 3,4-dichoro-5-fluorophenyl |
| 1.453 | cyclopropyl | 4,5-dichloro-2-fluorophenyl |
| 1.454 | cyclopropyl | 2-chloro-3,4-difluorophenyl |
| 1.455 | cyclopropyl | 2-chloro-4,5-difluorophenyl |
| 1.456 | cyclopropyl | 2-chloro-4,6-difluorophenyl |
| 1.457 | cyclopropyl | 3-chloro-4,5-difluorophenyl |
| 1.458 | cyclopropyl | 3,4-methylenedioxyphenyl |
| 1.459 | cyclopropyl | benzo[1,3]diox-5-yl |
| 1.460 | cyclopropyl | 2,3-dihydrobenzo[1,4]dioxin-6-yl |
| 1.461 | cyclopropyl | 2-naphthyl |
| 1.462 | cyclopropyl | 2-pyridyl |
| 1.463 | cyclopropyl | 3-pyridyl |
| 1.464 | cyclopropyl | 4-pyridyl |
| 1.465 | cyclopropyl | 3-chloropyridin-2-yl |
| 1.466 | cyclopropyl | 4-chloropyridin-2-yl |
| 1.467 | cyclopropyl | 5-chloropyridin-2-yl |
| 1.468 | cyclopropyl | 6-chloropyridin-2-yl |
| 1.469 | cyclopropyl | 2-chloropyridin-3-yl |
| 1.470 | cyclopropyl | 4-chloropyridin-3-yl |
| 1.471 | cyclopropyl | 2-chloropyridin-4-yl |
| 1.472 | cyclopropyl | 3-chloropyridin-4-yl |
| 1.473 | cyclopropyl | 2-chloropyridin-5-yl |
| 1.474 | cyclopropyl | 3-chloropyridin-5-yl |
| 1.475 | cyclopropyl | 3-methylpyridin-2-yl |
| 1.476 | cyclopropyl | 4-methylpyridin-2-yl |
| 1.477 | cyclopropyl | 5-methylpyridin-2-yl |
| 1.478 | cyclopropyl | 6-methylpyridin-2-yl |
| 1.479 | cyclopropyl | 2-methylpyridin-3-yl |
| 1.480 | cyclopropyl | 4-methylpyridin-3-yl |
| 1.481 | cyclopropyl | 2-methylpyridin-4-yl |
| 1.482 | cyclopropyl | 3-methylpyridin-4-yl |
| 1.483 | cyclopropyl | 2-methylpyridin-5-yl |
| 1.484 | cyclopropyl | 3-methylpyridinyl-5-yl |
| 1.485 | cyclopropyl | 2-trifluoromethylpyridin-5-yl |
| 1.486 | cyclopropyl | 3-trifluoromethylpyridin-5-yl |
| 1.487 | cyclopropyl | 2,6-dichloropyridin-3-yl |
| 1.488 | cyclopropyl | 2-chloro-4-methylpyridin-5-yl |
| 1.489 | cyclopropyl | 6-chloro-2-methylpyridin-3-yl |
| 1.490 | cyclopropyl | 5-chlorothiophen-2-yl |
| 1.491 | cyclopropyl | 2-chlorothiophen-3-yl |
| 1.492 | cyclopropyl | 2,5-dichlorothiophen-3-yl |
| 1.493 | cyclopropyl | 1-methylpyrazol-4-yl |
| 1.494 | cyclopropyl | 4-chloropyrazol-1-yl |

Table 2 covers 494 compounds of the type A-1, wherein G is hydrogen, $R^3$, $R^4$ and $R^5$ are hydrogen, $R^6$ is methyl, and $R^1$ and $R^2$ are as defined in Table 1.

Table 3 covers 494 compounds of the type A-1, wherein G is hydrogen, $R^3$ and $R^4$ are hydrogen, $R^5$ and $R^6$ are methyl, and $R^1$ and $R^2$ are as defined in Table 1.

Table 4 covers 494 compounds of the type A-1, wherein G is hydrogen, $R^3$ and $R^5$ are hydrogen, $R^4$ and $R^6$ are methyl, and $R^1$ and $R^2$ are as defined in Table 1.

Table 5 covers 494 compounds of the type A-1, wherein G is hydrogen, $R^3$ is hydrogen, $R^4$, $R^5$ and $R^6$ are methyl, and $R^1$ and $R^2$ are as defined in Table 1.

Table 6 covers 494 compounds of the type A-1, wherein G is hydrogen, $R^3$, $R^4$, $R^5$ and $R^6$ are methyl, and $R^1$ and $R^2$ are as defined in Table 1.

Table 7 covers 494 compounds of the type A-2

A-2 wherein G is hydrogen, $R^5$ and $R^6$ are hydrogen, and $R^1$ and $R^2$ are as defined in Table 1.

Table 8 covers 494 compounds of the type A-3

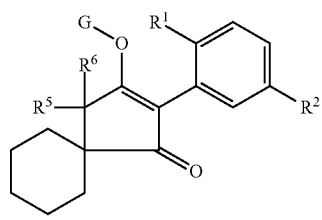

A-3 wherein G is hydrogen, $R^5$ and $R^6$ are hydrogen, and $R^1$ and $R^2$ are as defined in Table 1.

Table 9 covers 494 compounds of the type A-4

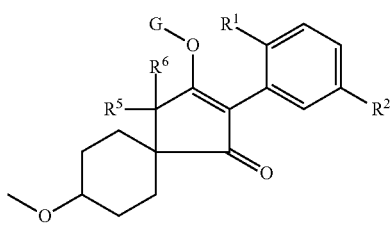

A-4 wherein G is hydrogen, $R^5$ and $R^6$ are hydrogen, and $R^1$ and $R^2$ are as defined in Table 1.

Table 10 covers 494 compounds of the type A-5

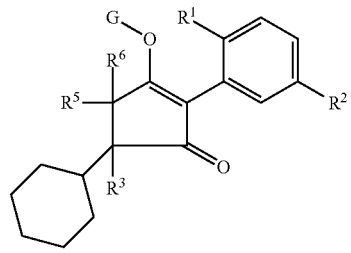

A-5 wherein G is hydrogen, $R^3$, $R^5$ and $R^6$ are hydrogen, and $R^1$ and $R^2$ are as defined in Table 1.

Table 11 covers 494 compounds of the type A-6

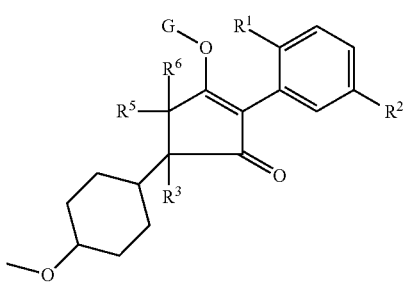

A-6 wherein G is hydrogen, $R^3$, $R^5$ and $R^6$ are hydrogen, and $R^1$ and $R^2$ are as defined in Table 1.

Table 12 covers 494 compounds of the type A-7

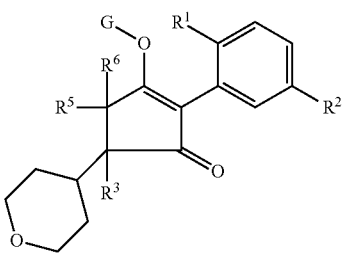

A-7 wherein G is hydrogen, $R^3$, $R^5$ and $R^6$ are hydrogen, and $R^1$ and $R^2$ are as defined in Table 1.

Table 13 covers 494 compounds of the type A-8

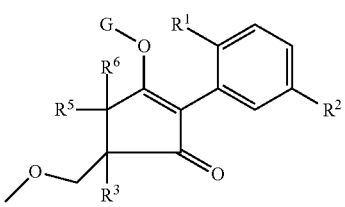

A-8 wherein G is hydrogen, $R^3$, $R^5$ and $R^6$ are hydrogen, and $R^1$ and $R^2$ are as defined in Table 1.

Table 14 covers 494 compounds of the type A-9, wherein G is hydrogen, $R^5$ and $R^6$ are hydrogen, and $R^1$ and $R^2$ are as defined in Table 1.

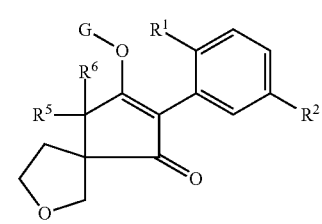

A-9

Table 15 covers 494 compounds of the type A-10

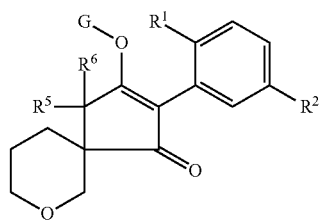

A-10 wherein G is hydrogen, $R^5$ and $R^6$ are hydrogen, and $R^1$ and $R^2$ are as defined in Table 1.

Table 16 covers 494 compounds of the type A-11

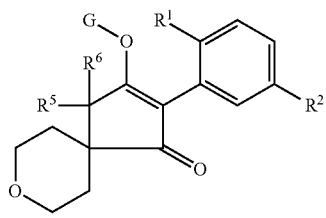

A-11 wherein G is hydrogen, $R^5$ and $R^6$ are hydrogen, and $R^1$ and $R^2$ are as defined in Table 1.

Table 17 covers 494 compounds of the type A-12

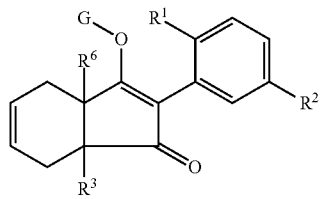

A-12 wherein G is hydrogen, $R^3$ and $R^6$ are hydrogen, and $R^1$ and $R^2$ are as defined in Table 1.

Table 18 covers 494 compounds of the type A-13

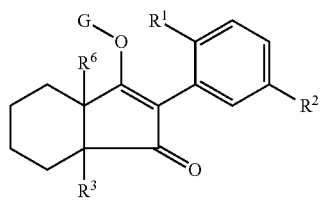

A-13 wherein G is hydrogen, $R^3$ and $R^6$ are hydrogen, and $R^1$ and $R^2$ are as defined in Table 1.

Table 19 covers 494 compounds of the type A-14

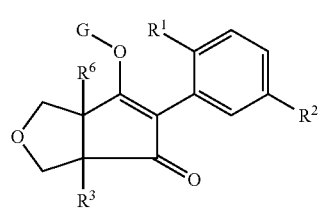

A-14 wherein G is hydrogen, $R^3$ and $R^6$ are hydrogen, and $R^1$ and $R^2$ are as defined in Table 1.

Table 20 covers 494 compounds of the type A-15

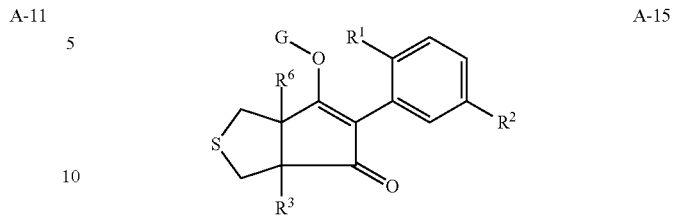

A-15 wherein G is hydrogen, $R^3$ and $R^6$ are hydrogen, and $R^1$ and $R^2$ are as defined in Table 1.

BIOLOGICAL EXAMPLES

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

Test plants: *Setaria faberi* (SETFA), *Lolium perenne* (LOLPE), *Alopecurus myosuroides* (ALOMY), *Echinochloa crus-galli* (ECHCG), and *Avena fatua* (AVEFA)

Pre-Emergence Activity

| Compound | Rate g/ha | LOLPE | ALOMY | ECHCG | AVEFA |
|---|---|---|---|---|---|
| T-1 | 250 | — | 90 | 100 | 70 |
| T-2 | 250 | 0 | 0 | 70 | 0 |
| T-3 | 250 | 90 | 30 | 100 | 60 |
| T-4 | 250 | 60 | 50 | 50 | 10 |
| T-5 | 250 | 20 | 20 | 20 | 0 |
| T-6 | 250 | 30 | 0 | 60 | 0 |
| T-7 | 250 | 10 | 0 | 20 | 0 |
| T-8 | 250 | 60 | 30 | 60 | 0 |
| T-9 | 250 | 80 | 60 | 90 | 50 |
| T-10 | 250 | 0 | 0 | 0 | 0 |
| T-11 | 250 | 30 | 20 | 50 | 10 |
| T-12 | 250 | 50 | 40 | 50 | 30 |
| T-13 | 250 | 0 | 0 | 0 | 0 |
| T-14 | 250 | 30 | 10 | 50 | 0 |
| T-15 | 250 | 0 | 0 | 0 | 0 |
| T-16 | 250 | 20 | 0 | 50 | 0 |
| T-17 | 250 | 60 | 40 | 80 | 0 |
| T-18 | 250 | 30 | 50 | 50 | 30 |
| T-19 | 250 | 20 | 0 | 10 | 0 |
| T-20 | 250 | 10 | 0 | 30 | 0 |
| T-21 | 250 | 100 | 40 | 40 | 10 |
| T-22 | 250 | 10 | 0 | 30 | 0 |
| T-23 | 250 | 30 | 20 | 50 | 0 |
| T-24 | 250 | 50 | 0 | 80 | 0 |

Post-Emergence Activity

| Compound | Rate g/ha | LOLPE | ALOMY | ECHCG | AVEFA |
|---|---|---|---|---|---|
| T-1 | 250 | — | 80 | 100 | 90 |
| T-2 | 250 | 0 | 20 | 100 | 80 |

-continued

| Compound | Rate g/ha | LOLPE | ALOMY | ECHCG | AVEFA |
|---|---|---|---|---|---|
| T-3 | 250 | 40 | 30 | 100 | 90 |
| T-4 | 250 | 30 | 50 | 70 | 0 |
| T-5 | 250 | 50 | 30 | 70 | 20 |
| T-6 | 250 | 60 | 50 | 90 | 10 |
| T-7 | 250 | 30 | 10 | 20 | 10 |
| T-8 | 250 | 60 | 50 | 100 | 30 |
| T-9 | 250 | 60 | 30 | 100 | 60 |
| T-10 | 250 | 40 | 30 | 90 | 50 |
| T-11 | 250 | 50 | 60 | 90 | 30 |
| T-12 | 250 | 50 | 50 | 90 | 50 |
| T-13 | 250 | 40 | 10 | 60 | 0 |
| T-14 | 250 | 30 | 30 | 70 | 30 |
| T-15 | 250 | 30 | 10 | 30 | 0 |
| T-16 | 250 | 60 | 50 | 80 | 80 |
| T-17 | 250 | 50 | 50 | 70 | 40 |
| T-18 | 250 | 70 | 80 | 100 | 90 |
| T-19 | 250 | 60 | 60 | 70 | 20 |
| T-20 | 250 | 20 | 20 | 70 | 10 |
| T-21 | 250 | 30 | 30 | 40 | 20 |
| T-22 | 250 | 10 | 30 | 60 | 10 |
| T-23 | 250 | 20 | 50 | 80 | 0 |
| T-24 | 250 | 50 | 30 | 100 | 10 |

What is claimed is:
1. Compounds of formula

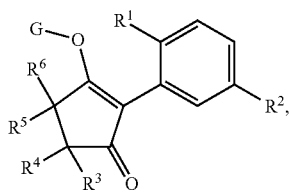

(I)

wherein
R$^1$ is ethyl, difluoromethoxy, trifluoromethoxy or cyclopropyl;
R$^2$ is optionally substituted aryl or optionally substituted heteroaryl; wherein, when present, the optional substituents on aryl and heteroaryl are selected, independently, from halogen, nitro, cyano, rhodano, isolhiocyanato, C$_{1-6}$ alkyl, C$_{1-6}$ haloalkyl, C$_{1-6}$ alkoxy-(C$_{1-6}$)alkyl, C$_{2-6}$ alkenyl, C$_{2-6}$ haloalkenyl, C$_{2-6}$ alkynyl, C$_{3-7}$ cycloalkyl (itself optionally substituted with C$_{1-6}$ alkyl or halogen), C$_{5-7}$ cycloalkenyl (itself optionally substituted with C$_{1-6}$ alkyl or halogen), hydroxy, C$_{1-10}$ alkoxy, C$_{1-10}$ alkoxy (C$_{1-10}$)alkoxy, tri(C$_{1-4}$)alkylsilyl(C$_{1-6}$)alkoxy, C$_{1-6}$ alkoxycarbonyl(C$_{1-10}$)alkoxy, C$_{1-10}$ haloalkoxy, aryl (C$_{1-4}$)alkoxy (where the aryl group is optionally substituted with halogen or C$_{1-6}$ alkyl), C$_{3-7}$ cycloalkyloxy (where the cycloalkyl group is optionally substituted with C$_{1-6}$ alkyl or halogen), C$_{3-10}$ alkenyloxy, C$_{3-10}$ alkynyloxy, mercapto, C$_{1-10}$ alkylthio, C$_{1-10}$ haloalkylthio, aryl(C$_{1-4}$)alkylthio, C$_{3-7}$ cycloalkylthio (where the cycloalkyl group is optionally substituted with C$_{1-6}$ alkyl or halogen), tri(C$_{1-4}$)-alkylsilyl(C$_{1-6}$)-alkylthio, arylthio, C$_{1-6}$ alkylsulfonyl, C$_{1-6}$ haloalkylsulfonyl, C$_{1-6}$ alkylsulfinyl, C$_{1-6}$ haloalkylsulfinyl, arylsulfonyl, tri (C$_{1-4}$)alkylsilyl, aryldi(C$_{1-4}$)-alkylsilyl, (C$_{1-4}$)alkyldiarylsilyl, triarylsilyl, C$_{1-10}$ alkylcarbonyl, HO$_2$C, C$_{1-10}$ alkoxycarbonyl, aminocarbonyl, C$_{1-6}$ alkylaminocarbonyl, di(C$_{1-6}$ alkyl)-aminocarbonyl, N—(C$_{1-3}$ alkyl)-N—(C$_{1-3}$ alkoxy)-aminocarbonyl, C$_{1-6}$ alkylcarbonyloxy, arylcarbonyloxy, di(C$_{1-6}$)alkylamino-carbonyloxy, aryl (itself optionally substituted with C$_{1-6}$ alkyl or halogen), heteroaryl (itself optionally substituted with C$_{1-6}$ alkyl or halogen), heterocyclyl (itself optionally substituted with C$_{1-6}$ alkyl or halogen), aryloxy (where the aryl group is optionally substituted with C$_{1-6}$ alkyl or halogen), heteroaryloxy (where the heteroaryl group is optionally substituted with C$_{1-6}$ alkyl or halogen), heterocyclyloxy (where the heterocyclyl group is optionally substituted with C$_{1-6}$ alkyl or halogen), amino, C$_{1-6}$ alkylamino, di(C$_{1-6}$)alkylamino, C$_{1-6}$ alkylcarbonylamino, N—(C$_{1-6}$)alkylcarbonyl-N—(C$_{1-6}$)alkylamino and arylcarbonyl (where the aryl group is itself optionally substituted with halogen or C$_{1-6}$ alkyl);

or two adjacent positions on an aryl or heteroaryl system are cyclised to form a 5, 6 or 7 membered carbocyclic or heterocyclic ring, itself optionally substituted with halogen or C$_{1-6}$ alkyl;

R$^3$, R$^4$, R$^5$ and R$^6$ are independently of each other, hydrogen, C$_1$-C$_4$alkyl, C$_2$-C$_4$alkenyl, C$_2$-C$_4$alkynyl, C$_1$-C$_3$haloalkyl, C$_2$-C$_4$haloalkenyl, C$_1$-C$_3$alkoxyC$_1$-C$_3$alkyl, C$_1$-C$_3$alkylthioC$_1$-C$_3$alkyl, C$_1$-C$_3$alkylsulfinylC$_1$-C$_3$alkyl, C$_1$-C$_3$alkylsulfonyl C$_1$-C$_3$alkyl, C$_3$-C$_6$cycloalkyl in which a methylene group is optionally replaced by an oxygen or sulfur atom and wherein the ring is optionally substituted once or twice by halogen, C$_1$-C$_2$alkyl or C$_1$-C$_2$alkoxy, or C$_3$-C$_6$cycloalkylC$_1$-C$_3$alkyl optionally substituted once or twice by halogen, C$_1$-C$_2$alkyl or C$_1$-C$_2$alkoxy;

or R$^3$ and R$^4$, or R$^5$ and R$^6$, together with the carbon atoms to which they are attached form a three- to seven-membered carbocyclic ring, in which a methylene group is optionally replaced by an oxygen or sulfur atom and wherein the ring is optionally substituted once or twice by halogen, C$_1$-C$_2$alkyl or C$_1$-C$_2$alkoxy;

or R$^4$ and R$^5$, together with the carbon atoms to which they are attached form a three- to seven-membered saturated carbocyclic ring, in which a methylene group is optionally replaced by an oxygen or sulfur atom and wherein the ring is optionally substituted once or twice by halogen, C$_1$-C$_2$alkyl or C$_1$-C$_2$alkoxy;

or R$^4$ and R$^5$, together with the carbon atoms to which they are attached form a five- to seven-membered unsaturated carbocyclic ring, wherein the ring is optionally substituted once or twice by halogen, C$_1$-C$_2$alkyl or C$_1$-C$_2$alkoxy;

and

G is hydrogen or an agriculturally acceptable metal, ammonium, sulfonium or latentiating group;

wherein, when G is a latentiating group, then G is selected from the groups —C(X$^a$)—R$^a$, C(X$^b$)—X$^c$—R$^b$, C(X$^d$)—N(R$^c$)—R$^d$, —SO$_2$—R$^e$, —P(X$^e$)(R$^f$)—R$^g$ and CH$_2$—X$^f$—R$^h$;

wherein X$^a$, X$^b$, X$^c$, X$^d$, X$^e$ and X$^f$ are independently of each other oxygen or sulfur; and wherein R$^a$ is H, C$_1$-C$_{18}$alkyl, C$_2$-C$_{18}$alkenyl, C$_2$-C$_{18}$alkynyl, C$_1$-C$_{10}$haloalkyl, C$_1$-C$_{10}$cyanoalkyl, C$_1$-C$_{10}$nitroalkyl, C$_1$-C$_{10}$aminoalkyl, C$_1$-C$_5$alkylaminoC$_3$-C$_5$alkyl, C$_2$-C$_8$dialkylaminoC$_1$-C$_5$alkyl, C$_3$-C$_7$cycloalkylC$_1$-C$_5$alkyl, C$_1$-C$_5$alkoxyC$_1$-C$_5$alkyl, C$_3$-C$_5$alkenyloxyC$_1$-C$_5$alkyl, C$_3$-C$_5$alkynylC$_1$-C$_5$oxyalkyl, C$_1$-C$_5$alkylthioC$_1$-C$_5$alkyl, C$_1$-C$_5$alkylsulfinylC$_1$-C$_5$alkyl, C$_1$-C$_5$alkylsulfonylC$_1$-C$_5$alkyl, C$_2$-C$_8$alkylideneaminoxyC$_1$-C$_5$alkyl, C$_1$-C$_5$alkylcarbonylC$_1$-C$_5$alkyl, C$_1$-C$_5$alkoxycarbonylC$_1$-C$_5$alkyl, aminocarbonylC$_1$-C$_5$alkyl, C$_1$-C$_5$alkylaminocarbonylC$_1$-C$_5$alkyl, C$_2$-C$_8$dialkylaminocarbonylC$_1$-C$_5$alkyl, C$_1$-C$_5$alkylcarbonylaminoC$_1$-C$_5$alkyl, N—C$_1$-

$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_1$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_1$-$C_5$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_5$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or $C_3$-$C_7$cycloalkylamino, di-$C_3$-$C_7$cycloalkylamino or $C_3$-$C_7$cycloalkoxy;

or $R^c$ and $R^d$ are joined together to form a 3-7 membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_1$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-

$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

and wherein the term "aryl" refers to phenyl or naphthyl; and the term "heteroaryl" refers to an aromatic ring system containing at least one heteroatom and consisting either of a single ring or of two fused rings.

2. A compound according to claim 1, wherein $R^1$ is ethyl.

3. A compound according to claim 1, wherein $R^2$ is optionally substituted phenyl or optionally substituted pyridyl.

4. A compound according to claim 3, wherein $R^2$ is phenyl substituted one to three times by fluorine, chlorine, bromine, methoxy, methyl, cyano or trifluoromethyl.

5. A compound according to claim 1, wherein $R^3$ and $R^4$ are, independently, hydrogen or $C_1$-$C_3$alkyl.

6. A compound according to claim 1, wherein $R^5$ and $R^6$ are independently of each other hydrogen, $C_1$-$C_3$alkyl, $C_1$-$C_3$alkoxy$C_1$-$C_3$alkyl, optionally substituted $C_3$-$C_6$cycloalkyl in which a ring carbon atom is optionally replaced by an oxygen or sulfur atom and wherein the ring is optionally substituted once or twice by $C_1$-$C_2$ alkyl or $C_1$-$C_2$ alkoxy, or $R^5$ and $R^6$ together with the carbon atom to which they are attached form an optionally substituted three- to seven membered carbocyclic ring, in which a ring carbon atom is optionally replaced by an oxygen or sulfur atom and wherein the ring is optionally substituted once or twice by $C_1$-$C_2$alkyl or $C_1$-$C_2$ alkoxy.

7. A compound according to claim 6, wherein $R^5$ and $R^6$ are independently of each other hydrogen, $C_1$-$C_3$alkyl, $C_1$-$C_3$alkoxy$C_1$-$C_3$alkyl, or $R^5$ and $R^6$ together with the carbon atom to which they are attached form an optionally substituted five- or six-membered carbocyclic ring, in which a ring carbon atom is optionally replaced by an oxygen atom, and wherein the ring is optionally substituted once or twice by $C_1$-$C_2$alkyl or $C_1$-$C_2$ alkoxy.

8. A compound according to claim 1, wherein G is hydrogen, an alkali metal or alkaline earth metal or a latentiating group.

9. A compound according to claim 8, wherein G is hydrogen.

10. A compound according to claim 1, wherein $R^1$ is ethyl, trifluoromethoxy or cyclopropyl, $R^2$ is phenyl substituted one to three times by fluorine, chlorine, bromine, methoxy, methyl or trifluoromethyl, or is naphthyl, $R^3$, $R^4$, $R^5$ and $R^6$ are hydrogen, or $R^5$ and $R^6$ together with the carbon atom to which they are attached form an optionally substituted three- to seven membered carbocyclic ring, in which a ring carbon atom is optionally replaced by a sulfur atom.

11. A herbicidal composition, which, in addition to comprising formulation assistants, comprises a herbicidally effective amount of a compound of formula I as defined in claim 1.

12. A composition according to claim 11, which, in addition to comprising the compound of formula I, comprises a further herbicide as mixing partner and, optionally, a safener.

13. A method of controlling grasses and weeds in crops of useful plants, which comprises applying a herbicidally effective amount of a compound of formula I as defined in claim 1, or of a composition comprising such a compound, to the plants or to the locus thereof.

* * * * *